(12) United States Patent
Schwartz et al.

(10) Patent No.: US 8,541,555 B2
(45) Date of Patent: Sep. 24, 2013

(54) HYDRAZONE-BASED AND OXIME-BASED FLUORESCENT AND CHROMOPHORIC/PRO-FLUORESCENT AND PRO-CHROMOPHORIC REAGENTS AND LINKERS

(75) Inventors: David A. Schwartz, Encinitas, CA (US); Leopoldo Mendoza, San Diego, CA (US)

(73) Assignee: Solulink Biosciences, Inc., San Diego, CA (US)

( * ) Notice: Subject to any disclaimer, the term of this patent is extended or adjusted under 35 U.S.C. 154(b) by 1451 days.

(21) Appl. No.: 11/787,932

(22) Filed: Apr. 18, 2007

(65) Prior Publication Data

US 2008/0221343 A1     Sep. 11, 2008

Related U.S. Application Data

(60) Provisional application No. 60/792,821, filed on Apr. 18, 2006, provisional application No. 60/792,822, filed on Apr. 18, 2006.

(51) Int. Cl.
- C07K 16/00 (2006.01)
- C07H 21/04 (2006.01)
- C07D 235/02 (2006.01)

(52) U.S. Cl.
USPC .... 530/391.3; 536/24.3; 546/255; 548/302.7; 548/300.1

(58) Field of Classification Search
USPC .... 546/1, 255; 548/302.7, 300.1; 530/391.3; 536/24.3
See application file for complete search history.

(56) References Cited

U.S. PATENT DOCUMENTS

| | | | |
|---|---|---|---|
| 5,130,446 A | 7/1992 | Musso et al. | |
| 5,420,285 A | 5/1995 | Schwartz et al. | |
| 5,491,224 A | 2/1996 | Bittner et al. | |
| 5,753,520 A | 5/1998 | Schwartz et al. | |
| 6,686,461 B1 | 2/2004 | Schwartz et al. | |
| 7,102,024 B1 | 9/2006 | Schwartz et al. | |
| 7,381,818 B2 * | 6/2008 | Lokhov et al. | 536/24.3 |
| 7,732,628 B2 | 6/2010 | Schwartz et al. | |
| 2005/0192430 A1 * | 9/2005 | Rosenthal et al. | 530/391.3 |

OTHER PUBLICATIONS

Rod-length dependent aggregation in a series of oligo(p-benzamide)-block-poly(ethylene glycol) rod-coil copolymers. Macromolecular Chemistry and Physics (2005), 206(20), 2067-2074 COEN: MCHPES; ISSN: 1022-1352; English.*

Ahn et al., Use of Fluorescein Hydrazide and Fluorescein Thiosemicarbazide Reagents for the Fluorometric Determination of Protein Carbonyl Groups and for the Detection of Oxidized Protein on Polyacrylamide Gels, Analytical Biochemistry, 161, 245-57, 1987.

Proudnikov et al., Chemical Methods of DNA and RNA Fluorescent Labeling, Nucleic Acids Research, 24 (22), 4535-42, 1996.

Wong et al., Photochromism of Quinolylhydrazones, Tetrahedron Letters, 44, 4593-96, 1968.

Schwartz et al., Technetium-99m-Human Polyclonal IgG Radiolabled via the Hydrazino Nicotinamide Derivative for Imaging Focal Sites of Infection in Rats, The Journal of Nuclear Medicine, 31 (12), 2022-28, 1990.

Schwartz, et al., Preparation of Hydrazino-Modified Proteins and Their Use for the Synthesis of 99m TC-Protein Conjugates, Bioconjugate Chemical, 2, 333-36, 1991.

Nitta et al., Cross-Linking Between 16S Ribosomal RNA and Protein S4 in *Escherichia coli* Ribosomal 30S Subunits Effected by Treatment with Bisulfite/Hydrazine and Bromopyruvate, Eur. J. Biochem., 157, 427-32, 1986.

Heitzmann et al., Use of the Avidin-Biotin Complex for Specific Staining of Biological Membranes in Electron Microscopy, Proc. Natl. Acad. Sci. USA, 71 (9), 3537-41, 1974.

Diamandis et al, The Biotin-(Strept)Avidin System: Principles and Applications in Biotechnology, Clin. Chem., 37 (5), 625-36, 1991.

Wilchek et al, Avidin-Biotin Technology, Methods in Enzymology, 184, 608-12, 1990.

Savage et al., Avidin-Biotin Chemistry: A Handbook. Rockford, Ill., Pierce Chemical Co. 1992.

Green, Biochem. J., 94, 23c-24c, 1965.

Ryan, et al., Ligand Structure and Fluorescence of Metal Chelates; N-Heterocyclic Hydrazones with Zinc, Analytica Chimica Acta, 58, 101-06, 1972.

Negishi et al., $N^4$-Aminocytidine, a Nucleoside Analog that has an Exceptionally High Mutagenic Activity, Nucleic Acids Research, 11 (15), 5223-33, 1983.

Mishra et al., Cyanines during the 1990's: A Review, Chemical Reviews, 100, 1973-2011, 2000.

Arterburn et al., Organic Letters, 3 (9), 1351-54, 2001.

Arterburn et al Chemical Communications, 15, 1890-91, 2003.

\* cited by examiner

*Primary Examiner* — Paul V. Ward
(74) *Attorney, Agent, or Firm* — Jones Day

(57) ABSTRACT

Conjugationally extended hydrazine compositions of the formula $(RR_2)N(H)_n(NH_2)_n$, fluorescent hydrazone compositions of the formula $(RR_2)NN=C(R_1R_2)$, methods of the formation of hydrazones from the reaction of conjugationally extended hydrazines with conjugationally extended carbonyls and methods of their use in assays systems are described. Use of these conjugationally extended hydrazine and oxime compositions for direct calorimetric and fluorometric assays wherein a chromophore or the fluorophore is incorporated into the linker that is positioned between a reactive linking moiety and a biotin molecule. More specifically the linker comprises one molecule of a high affinity binding pair such as for example biotin of the biotin/avidin high affinity binding pair, connected to a spacer molecule such as for example a length of polyethyleneglycol followed by a pro-chromophoric, chromophoric, pro-fluorescent or fluorescent moiety connected to an amino-, thiol- or carbohydrate-reactive moiety such as for example succinimidyl, maleimido or aminoxy group respectively, that may covalently link to a biomolecule.

24 Claims, 24 Drawing Sheets

HYDRAZONE-BASED AND OXIME-BASED FLUORESCENT AND CHROMOPHORIC/PRO-FLUORESCENT AND PRO-CHROMOPHORIC REAGENTS AND LINKERS

CROSS-REFERENCE TO RELATED APPLICATIONS

This application is a regular application claiming priority from provisional patent application Ser. No. 60/792,821 and 60/792,822 both filed 18 Apr. 2006.

STATEMENT REGARDING FEDERALLY SPONSORED RESEARCH OR DEVELOPMENT

None

INCORPORATION-BY-REFERENCE OF MATERIAL SUBMITTED ON COMPACT DISC

None

BACKGROUND OF THE INVENTION (1) Field of the Invention

The present invention relates to compounds used to label biomolecules for diagnostic and therapeutic purposes. In particular, it relates to fluorescent, chromophoric, pro-fluorescent and pro-chromophoric compounds that may be conjugated to biomolecules such as proteins and nucleic acids. Such compounds may be incorporated into linkers that may be used to link a ligand to a biomolecular probe allowing quantitation of the ligand bound to that molecular probe.

(2) Description of Related Art

Methods to detect interactions between biomolecules continues to be an area of active research as new and more sensitive methods are required to increase sensitivity, reduce costs and enable new detection methods. One of the most widely used methods is to directly label a biomolecule with a fluorescent molecule that fluoresces at a desired frequency. For example, a fluorescent molecule is modified with a thiol- or amino-reactive moiety such as succinimidyl esters or maleimides that form a covalent bound in the presence of a sulhydryl or amine group of a desired protein. The modified fluorescent molecule is isolated and reacted with the desired protein. The fluorescently labeled protein is then used to detect a desired target by monitoring the unique fluorescent frequency of the fluorophore. A variety of fluorophores have been modified with these moieties including fluorescein, rhodamine, Texas Red and cyanine dyes, Cy3 and Cy5. Unfortunately, the conjugation methods often cause quenching and photobleaching of the fluorophore and there can be interference with the observed signal if the unbound labeled biomolecule is not removed from the reaction mixture.

Other biolmolecules such as nucleic acids such as DNA, RNA, polynucleotide and oligonucleotides have been labeled with fluorophores is commonly accomplished by incorporating a fluorophore on the base moiety of a nucleoside triphosphate. These fluorescently labeled triphosphates are added to the polymerase chain reaction (PCR) or reverse transcription reaction wherein the labeled nucleoside is incorporated in the amplicon yielding a fluorescently labeled polynucleotide. These fluorescently labeled polynucleotides are probed using oligonucleotide microarrays identifying sequences present in the target. Unfortunately, the fluorophores used for labeling these biomolecules are not often stable to these synthesis conditions. In addition, the long-term stability of conjugates are low due to photobleaching, consequently, retention of the fluorescent signal is difficult when archiving microarrays.

A variety of references cite the use of fluorescent hydrazides, thiosemicarbazides and hydrazides to react with aldehydes on biological molecules for the detection of the aldehydes. For example Ahn et al. (B. Ahn, S. G. Rhee and E. R. Stadtman, Anal. Biochem. 161:245 (1987) describe the use of fluorescein hydrazide and fluorescein thiosemicarbazide for the fluorometric determination of protein carbonyl groups and for the detection of oxidized proteins on polyacrylamide gels. Proudnikov and Mirzabekov (Nucl. Acids Res. 24:4535 (1996)) describe labeling of DNA and RNA to identify acid-induced depurination that results in production of aldehyde moieties detected by reaction of fluorescent labels containing hydrazide groups in the presence of sodium cyanoborohydride. Others have labeled the reducing end of polysaccharides with fluorescent hydrazides. These methods are used to detect aliphatic aldehyde groups on biomolecules. In each of the references the fluorescent moiety is incorporated on the hydrazine or hydrazide that forms a hydrazone on reaction with the aldehyde present on the biomolecule.

It has been documented that hydrazones formed between certain aromatic aldehydes and aromatic hydrazines and not aromatic hydrazides or aromatic thiosemicarbazides form fluorescent molecules (J. Wong and F. Bruscato, Tet. Lett. 4593, 1968). It has also been reported that hydrazones formed specifically from 2-substituted aldehyde heterocycles and 2-substituted hydrazine heterocycles become fluorescent on chelation to zinc (D. E. Ryan, F. Snape and M. Winpe, Anal. Chim. Acta 58:101, 1972).

Schwartz et at (U.S. Pat. No. 5,420,285; U.S. Pat. No. 5,753,520; U.S. Pat. No. 5,420,285; J. Nucl. Med. 31(12): 2022, 1990 and Bioconjug. Chem. 2(5):333, 1991) describe the preparation of succinimidyl 6-hydraziniumnicotinate hydrochloride for the one-step modification of amino groups on proteins and other molecules to incorporate pyridylhydrazine moieties on proteins for the specific purpose of binding technetium-99m for in vivo diagnostic purpose. Subsequently Schwartz (U.S. patent application Ser. No. 09/630, 060) describe novel oligonucleotide aldehyde and hydrazine phosphoramidite reagents for incorporation of aldehydes and hydrazines on synthetic oligonucleotides including aromatic and heteroaromatic aldehydes and hydrazines. Triphosphates incorporating both aromatic hydrazine and aromatic aldehydes have been described by Schwartz and Hogrefe (U.S. Pat. No. 6,686,461).

Cytidine and deoxycytidine moieties in polynucleotides can be transformed into 4-N-aminocytidine (4-hyd-C), an aromatic hydrazine, by treatment with hydrazine/bisulfite at neutral pH. Nitta et al. Eur. J. Biochem. 157(2):427, 1986 has described crosslinking between 16S ribosomal RNA and protein S4 in *E. coli* ribosomal 30S subunits effected by treatment with bisulfite/hydrazine and bromopyruvate. Also Musso et al., (U.S. Pat. No. 5,130,446) describe labeling of 4-N-aminocytidine moieties on hydrazine/bisulfite treated DNA to yield a fluorescently labeled polynucleotide. Bittner et al. (U.S. Pat. No. 5,491,224) also describe the labeling of transaminated DNA with fluorescent moieties possessing moieties that react with the transaminated cytosine such as fluorophores possessing succinimidyl esters.

In all of the aforementioned references the biomolecule is fluorescently labeled with a fluorescent molecule. Unfortunately as previously stated the processes or methods used to prepare the conjugate can often times cause quenching or photobleaching of the fluorophore. In addition, during use the unbound fluorescently labeled conjugate must be removed to obtain an accurate fluorescent signal.

Therefore, there is a need in the field for a fluorescent label that is resistant to reaction conditions necessary for producing a labeled biomolecule and does not require removal of the unbound fluorescently labeled biomolecule from the detection reaction mixture to obtain a accurate and/or quantitative signal. There is also a need for fluorophores that may be formed under standard assay conditions from pro-fluorophores which, are stable under various laboratory conditions and by a reaction that is highly specific and efficient.

To date the most commonly used method to link, immobilize and detect biomolecules is the biotin/streptavidin ligand/receptor couple. Biotin (FIG. 1) is a small molecule, MW 250, that binds to streptavidin with an association constant of $10^{15}$. The extremely high binding constant and fast kinetics of binding and the stability of avidin under a variety of conditions make this an ideal ligand/receptor pair for these purposes. Biotin has been modified to include amino, thiol and carbohydrate reactive moieties, i.e. succinimidyl ester, maleimido and hydrazide respectively, to allow easy incorporation into a large variety of biomolecules. To accomplish detection of an analyte, biotin is conjugated to a probing biomolecule such as an antibody or an oligonucleotide. Following binding of the biotinylated biomolecule to its receptor or complement, an avidin/reporter conjugate such as an avidin/fluorophore conjugate or a avidin/reporter enzyme conjugate is added and allowed to bind to biotinylated probe and visualized by fluorescence detection or addition of a substrate that emits light or precipitates a colored insoluble product on enzymatic processing (Heitzmann H., Richards F. M., Proc. Natl. Acad. Sci. USA 71:3537-3541, 1974; Diamandis E. P., Christopoulos T. K., Clin. Chem. 37:625-636, 1991; Wilchek M. Methods Enzymol Vol. 184, 1990; Savage, M. D. et al., 1992 Avidin-Biotin Chemistry: A Handbook. Rockford, Ill.: Pierce Chemical Co.).

Following conjugation it is important to determine that the probe molecule has been biotinylated and to quantify the number of biotins now conjugated to the probe molecule. To this end two multi-step indirect assays have been developed. The first assay is the HABA ([2-(4'-hydroxyazobenzene)] benzoic acid) assay developed by Green (Green, N. M. Biochem. J., 94, 23c-24, 1965). To quantify biotin label incorporation, a solution containing the biotinylated protein is added to a mixture of HABA and avidin. Because of its higher affinity for avidin, biotin displaces the HABA from its interaction with avidin and the absorption at 500 nm decreases proportionately. By this method, an unknown amount of biotin present in a solution can be evaluated in a single cuvette by measuring the absorbance of the HABA-avidin solution before and after addition of the biotin-containing sample. The change in absorbance relates to the amount of biotin in the sample.

The second more sensitive fluorescence-based multi-step assay developed by Molecular Probes (recently acquired by Invitrogen Corporation in Carlsbad, Calif.) is the 'Fluoreporter Biotin Quantitation Assay' that is based on fluorescence resonance energy transfer (FRET) quenching wherein an avidin molecule is labeled with a fluorophore and its binding sites are occupied with a fluorescent molecule that quenches the covalently linked fluorophore until the quencher in the binding site is displaced by a higher binding biotin molecule resulting in fluorescence of the covalently attached fluorophore. While this assay is sensitive to 50-100 pmol range it requires many processing steps and a fluorimeter or multi-well fluorimeter. It is also recommended to digest the biotinylated protein prior to the assay to expose any sterically encumbered biotins.

Consequently there is a need in the field for a assay wherein the number of biotins covalently linked to a biomolecule could be determined by direct methods such as spectroscopic means.

BRIEF SUMMARY OF THE INVENTION

The present invention provides profluorescent/prochromophoric hydrazine and aldehyde reagent compounds for preparing novel hydrazone-based fluorescent molecules. More specifically conjugationally extended profluorescent/prochromophoric hydrazine compounds of the formula $(RR_2)N(H)_n(NH_2)_n$, wherein R is independently a substituted or unsubstituted conjugationally extended moiety wherein the unsubstituted conjugationally extended moiety is an alkenyl, alkynyl, aromatic, polyaromatic, heteroaromatic or polyheteroaromatic moiety and wherein the substituted conjugationally extended moiety may be substituted with any combination of one or more of the groups hydroxy, alkoxy, alkene, alkyne, nitro, carboxy, sulfo, unsubstituted amine and substituted primary, secondary, tertiary and quaternary amine; $R_2$ is independently a hydrogen, a straight chain aliphatic moiety of 1-10 carbon atoms, a branched aliphatic moiety of 1-10 carbon atoms, a cyclic aliphatic moiety of 1-10 carbon atoms, a substituted or unsubstituted conjugationally extended moiety wherein the unsubstituted conjugationally extended moiety is an alkenyl, alkynyl, aromatic, polyaromatic, heteroaromatic or polyheteroaromatic moiety and wherein the substituted conjugationally extended moiety may be substituted with any combination of one or more of the groups hydroxy, alkoxy, alkene, alkyne, nitro, carboxy, sulfo, unsubstituted amine and substituted primary, secondary, tertiary and quaternary amine; n is 0 when m is 2 and n is 1 when m is 1 may be combined with conjugationally extended profluorescent/prochromophoric carbonyl compounds of the formula $O=C(R_1R_2)$ wherein: $R_1$ is independently a substituted or unsubstituted conjugationally extended moiety wherein the unsubstituted conjugationally extended moiety is an alkenyl, alkynyl, aromatic, polyaromatic, heteroaromatic or polyheteroaromatic moiety and wherein the substituted conjugationally extended moiety may be substituted with any combination of one or more of the groups hydroxy, alkoxy, alkene, alkyne, nitro, carboxy, sulfo, unsubstituted amine and substituted primary, secondary, tertiary and quaternary amine; $R_2$ is independently a hydrogen, a straight chain aliphatic moiety of 1-10 carbon atoms, a branched aliphatic moiety of 1-10 carbon atoms, a cyclic aliphatic moiety of 1-10 carbon atoms, a substituted or unsubstituted conjugationally extended moiety wherein the unsubstituted conjugationally extended moiety is an alkenyl, alkynyl, aromatic, polyaromatic, heteroaromatic or polyheteroaromatic moiety and wherein the substituted conjugationally extended moiety may be substituted with any combination of one or more of the groups hydroxy, alkoxy, alkene, alkyne, nitro, carboxy, sulfo, unsubstituted amine and substituted primary, secondary, tertiary and quaternary amine; n is 0 when m is 2 and n is 1 when m is 1 to form fluorescent hydrazone compounds of the formula $(RR_2)NN=C(R_1R_2)$.

In one embodiment the hydrazone compound has the formula:

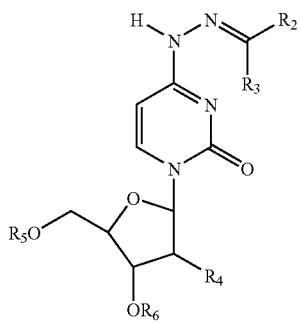

wherein $R_1$ (which is $R_2$) is independently a substituted or unsubstituted conjugationally extended moiety wherein the unsubstituted conjugationally extended moiety is an alkenyl, alkynyl, aromatic, polyaromatic, heteroaromatic or polyheteroaromatic moiety and wherein the substituted conjugationally extended moiety may be substituted with any combination of one or more of the groups hydroxy, alkoxy, alkene, alkyne, nitro, carboxy, sulfo, unsubstituted amine and substituted primary, secondary, tertiary and quaternary amine; $R_2$ (which is $R_3$) is independently a hydrogen, a straight chain aliphatic moiety of 1-10 carbon atoms, a branched aliphatic moiety of 1-10 carbon atoms, a cyclic aliphatic moiety of 1-10 carbon atoms, a substituted or unsubstituted conjugationally extended moiety wherein the unsubstituted conjugationally extended moiety is an alkenyl, alkynyl, aromatic, polyaromatic, heteroaromatic or polyheteroaromatic moiety and wherein the substituted conjugationally extended moiety may be substituted with any combination of one or more of the groups hydroxy, alkoxy, alkene, alkyne, nitro, carboxy, sulfo, unsubstituted amine and substituted primary, secondary, tertiary and quaternary amine; $R_3$ (which is $R_4$) is H or OH; $R_4$ (which is $R_6$) is H or a nucleic acid moiety; and $R_5$ (which is $R_7$) is $PO_3$ or a nucleic acid moiety.

In another embodiment these novel profluorophore hydrazine and carbonyl compounds may further comprise a linkable moiety at one of the R or $R_2$ positions wherein the linkable moiety is selected from the group consisting of an amino reactive moiety, a thiol reactive moiety, an ester moiety and a modified carbohydrate monomer moiety.

In yet another embodiment a biomolecule such as for example a nucleic acid, a nucleotide, a protein, an amino acid, a carbohydrate monomer or a polysaccharide is linked to the profluorescent/prochromophoric hydrazine and/or profluorescent/prochromophoric carbonyl by a linkable moiety. If the biomolecule is a nucleic acid it may be DNA, cDNA, RNA, or PNA and can comprise natural or unnatural bases or internucleotide linkages selected from the group consisting of phosphodiesters, phosphorothioates, phosphoramidites and peptide nucleic acids.

In still another embodiment one or more of the profluorescent/prochromophoric hydrazine or carbonyl compounds may be bound to a polymer such as poly-lysine, poly-ornithine or polyethyleneglycol by one or more linkable moieties.

In another aspect of the present invention methods of forming a hydrazone compound are provided by combining the conjugationally extended profluorescent/prochromophoric hydrazine of formula $(RR_2)N(H)_n(NH_2)$ with conjugationally extended profluorescent/prochromophoric carbonyl of the formula $O=C(R_1R_2)$ for a time and under conditions that allow hydrazone formation.

In one embodiment of this aspect of the invention the conjugationally extended profluorescent/prochromophoric hydrazine and/or the conjugationally extended profluorescent/prochromophoric carbonyl may further comprise a linkable moiety at either the $R_1$ or $R_2$ position.

In yet another aspect of the invention a method for labeling a biomolecule with a fluorescent hydrazone compound is provided.

In still another aspect the present invention provides oxyamine and aldehyde reagent compounds for preparing novel oxime-based fluorescent molecules. More specifically conjugationally extended profluorescent/prochromophoric oxyamine compound of formula: $(R_1R_2)ONH_2$ are provided wherein: $R_1$ is a substituted or unsubstituted conjugationally extended moiety wherein the unsubstituted conjugationally extended moiety is an alkenyl, alkynyl, aromatic, polyaromatic, heteroaromatic or polyheteroaromatic moiety and wherein the substituted conjugationally extended moiety may be substituted with any combination of one or more of the groups hydroxy, alkoxy, alkene, alkyne, nitro, carboxy, sulfo, unsubstituted amine and substituted primary, secondary, tertiary and quaternary amine; and $R_2$ is a hydrogen, a straight chain aliphatic moiety of 1-10 carbon atoms, a branched aliphatic moiety of 1-10 carbon atoms, a cyclic aliphatic moiety of 1-10 carbon atoms, a substituted or unsubstituted conjugationally extended moiety wherein the unsubstituted conjugationally extended moiety is an alkenyl, alkynyl, aromatic, polyaromatic, heteroaromatic or polyheteroaromatic moiety and wherein the substituted conjugationally extended moiety may be substituted with any combination of one or more of the groups hydroxy, alkoxy, alkene, alkyne, nitro, carboxy, sulfo, unsubstituted amine and substituted primary, secondary, tertiary and quaternary amine.

In one embodiment a profluorescent/prochromophoric oxyamine compound is provided wherein $R_1$ or $R_2$ further comprise a linkable moiety selected from the group consisting of an amino reactive moiety, a thiol reactive moiety, an ester moiety and a modified carbohydrate monomer moiety.

In another embodiment a profluorescent/prochromophoric oxyamine compound is provided wherein the linker further comprises a biomolecule selected from the group consisting of a nucleic acid, a nucleotide, a protein an amino acid, a carbohydrate monomer and a polysaccharide. The nucleic acid may be selected from the group consisting of DNA, cDNA, RNA and PNA and may comprise natural or unnatural bases or internucleotide linkages selected from the group consisting of phosphodiesters, phosphorothioates, phosphoramidites and peptide nucleic acids.

In another aspect of the invention a spectrophotometrically quantifiable linker is provided comprising of formula: A-B-C-D wherein A is an amino, thiol or carbohydrate reactive moiety; B is a chromophoric or fluorescent moiety; C is a flexible linker; and D is biotin or a receptor ligand. When A is an amino reactive moiety it may be selected from the group consisting of N-hydroxysuccinimidyl, p-nitrophenyl, pentafluorophenyl and N-hydroxybenzotriazolyl. When A is a thiol reactive moiety it may be selected from the group consisting of maleimido, α-haloacetamido and pyridylsulfides. When A is a carbohydate reactive moiety it may be aminooxy. B may be a compound that fluoresces, emits light or precipitates a colored insoluble product on enzymatic processing. C is a flexible linker and may be a PEG flexible linker having no less than 8 carbon atoms and no more than 34 carbon atoms. D is a receptor ligand selected from the group consisting of receptor ligand pairs biotin/avidin, peptide S/ribonuclease, complimentary oligonucleotide pairs or antibody/ligand pairs, and digoxigenin/anti-digoxigenin antibody.

In one embodiment of the present invention wherein the spectrophotometrically quantifiable linker is bound to a biomolecule via a amino, thiol or carbohydrate reactive moiety and wherein the biomolecule is selected from the group consisting of a protein, a peptide, an oligonucleotide and a polynucleotide. Alternatively the spectrophotometrically quantifiable linker may be bound to a biomolecule via receptor ligand pairs such as biotin/avidin, peptide S/ribonuclease, digoxigenin/anti-digoxigenin antibody complimentary oligonucleotide pairs or antibody/ligand pairs. Correspondingly, a first biomolecule may be bound via an amino, thiol or carbohydrate reactive moiety and a second biomolecule may be bound via a receptor ligand pair to the spectrophotometrically quantifiable linker.

In another aspect of the present invention a method of preparing a spectrophotometrically quantifiable linker is provided by the steps of preparing a first conjugate of a first biomolecule bound to one profluorescent/prochromophoric compound of a fluorescent pair via an amino, thiol or carbohydrate reactive moiety and preparing a second conjugate of a second biomolecule bound to a flexible linker via a biotin or a receptor ligand and the other profluorescent/prochromophoric compound of a fluorescent pair and combining the first conjugate with the second conjugate for a time thereby forming a hydrazone bond between the profluorescent/prochromophoric compound pair forming a fluorescent moiety.

DETAILED DESCRIPTION OF THE INVENTION

Figure 1:
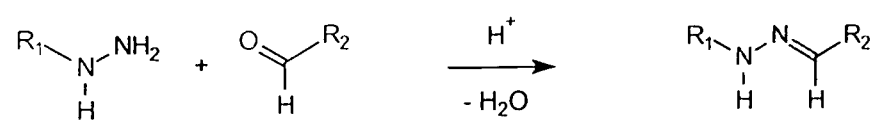
FIG. 1: A diagrammatic representation of the chemistry for the formation of fluorescent hydrazones from conjugationally extended aldehydes and hydrazines.

Unless defined otherwise, all terms used herein have the same meaning as are commonly understood by one of skill in the art to which this invention belongs. All patents, patent applications and publications referred to throughout the disclosure herein are incorporated by reference in their entirety. In the event that there is a plurality of definitions for a term herein, those in this section prevail.

The term "biomolecule" as used herein refers to a compound of biological origin, or of biological activity, that may have, or may be modified to have, an amine group or carbonyl group that may be harnessed in the formation of a hydrazone bond with a novel carbonyl profluorophore or novel hydrazine profluorophore of the present invention. Biomolecules include for example a nucleic acid, a nucleotide, a protein, an amino acid, a carbohydrate monomer and a polysaccharide. If the biomolecule is a nucleic acid it may be DNA, cDNA, RNA, or PNA and may comprise natural or unnatural bases or internucleotide linkages such as for example phosphodiesters, phosphorothioates, phosphoramidites or peptide nucleic acids.

The term "profluorophore" as used herein refers to a compound that may, or may not fluoresce, but when joined with its corresponding profluorophore pair compound produces a fluorescent hydrazone compound that has a peak emission wavelength substantially separate from the peak emission wavelength of either of the profluorophores that they may that make up the fluorescent hydrazone compound. A profluorophore pair comprises a hydrazine-based profluorophore and a carbonyl-based profluorophore that when combined form a fluorescent hydrazone compound.

The term "pro-chromophore" as used herein refers to a compound that may, or may not produce a visible color, but when joined with its corresponding pro-chromophoric pair compound produces a chromophoric compound that has a peak observable wavelength substantially separate from the peak observable wavelength of either of the prochromophores that make up the chromophoric hydrazone compound. A pro-chromophoric pair comprises a hydrazine-based pro-chromophore and a carbonyl-based pro-chromophore that when combined form a chromophoric hydrazone compound.

The term "reactive linking moiety" as used herein refers to molecules used commercially for binding one molecule to another based on the presence of a particular chemical group on the molecule of interest. Some commercially sold molecules referred to herein as linking moieties include those that react with free amines on the target molecule, such as N-hydroxysuccinimidyl, p-nitrophenyl, pentafluorophenyl and N-hydroxybenzotriazolyl ester and those that react with free sulfhydryls present on the target molecule such as maleimido, α-haloacetamido and pyridyldisulfides.

The term "ligand/receptor couple" as used herein refers to a pair of molecules having a substantially high affinity of binding specifically to one another. One example of such a binding pair would be a receptor on a cell and the ligand that binds that receptor. Another example would be biotin and avidin, which are two molecules that have a strong affinity for binding each other having an association constant of around $10^{15}$. Other pairs include Peptide S and ribonuclease A, digoxigenin and it receptor and complementary oligonucleotide pairs.

To achieve the optimal signal from a fluorescent label it is important that the structural integrity of the fluorophore is retained throughout processing of the labeled reporter molecule. A disadvantage with commercially available fluorophores is their propensity to be hydrolytically unstable or photobleach. The ability to efficiently form fluorescent species in situ in biological media in contrast to present methods wherein a labile fluorescent species is present throughout all protocols would be extremely advantageous in yielding products with fully retained fluorescence for improved limits of detection. In one current example in DNA microarays, fluorescently labeled triphosphates, e.g. Cy3 and Cy5 triphosphosphates (Amersham Biosciences, Piscataway, N.J.), are incorporated during PCR or reverse transcriptase amplification however quenching of the fluorophores through photobleaching or hydrolysis occurs during the many manipulations required to isolate the desired fluorescently labeled polynucleotide. To overcome this problem a less than ideal two-step method has been developed wherein a 3-aminoallylcytidine triphosphate is incorporated during polynucleotide amplification with subsequent purification, labeling with fluorescent succinimidyl esters and final purification to remove excess unincorporated fluorescent molecules. This chemistry is based on a amino/succinimidyl ester reaction that requires large excess of succinimidyl ester due to its instability in water and steps to remove the excess hydrolyzed reagent. This reaction proceeds over a small pH range, i.e. 7.2-8.0 and is concentration dependent.

It would be advantageous to have a method wherein a stable non-fluorescent species is used to label a biomolecule that following all required processing in techniques such as PCR, 2-dimensional electrophoresis or immunohistochemistry can be reacted efficiently with a second non-fluorescent molecule to form a fluorescent species. The present invention describes a chemistry wherein a conjugationally extended hydrazine reacts with a conjugationally extended carbonyl in situ in aqueous media to form a fluorescent molecule (FIG. 1). Both aldehydes and hydrazines are stable in aqueous media and react efficiently to form stable hydrazones. The hydrazone formation is acid catalyzed and has an optimum pH of 4.7 but proceeds up to pH 8.0. This methodology could be extended to use with biosensors for biowarfare and pathogen detection, brand security and Near-IR products. These fluorophores may also be engineered for use in laser and photonics applications.

Figure 2:
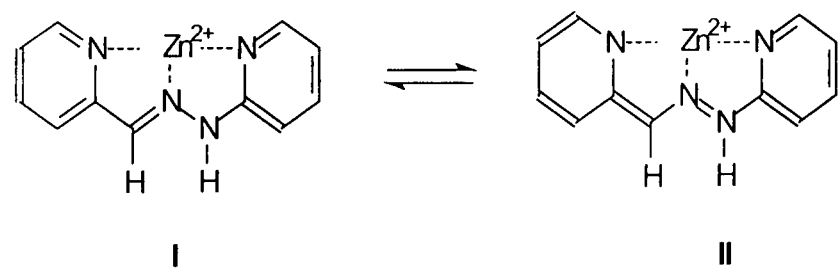
FIG. 2: A diagrammatic representation of the tautomerization of bis-(2-heteroaromatic)hydrazone chelates.

D. E. Ryan, F. Snape and M. Winpe (Ligand Structure and Fluorescence of Metal chelates; N-Heterocyclic Hydrazones with Zinc, Anal. Chim. Acta 58:101, 1972) described a series of hydrazone chelates (Table 1) and that upon addition of $Zn^{2+}$ the chelates complex the metal yielding a fluorescent metal chelate (FIG. 2). It was postulated how the non-complexed chelate can exist in two different tautomers that have different fluorescent properties due to disrupted aromatic bonding. The addition of the zinc ion 'locks in' the tautomer with better conjugation and higher fluorescence. These authors further described the use of these chelates as analytical tools for determination of trace amounts, i.e. parts per million and parts per billion, of zinc.

| Full Name | Abbreviated Form | $\lambda_{excitation}$ | $\lambda_{emission}$ | Relative Fluorescence* |
|---|---|---|---|---|
| Pyridine-2-aldehyde-2-pyridyl hydrazone | PAPH | 455 | 515 | 1 |
| Quinoline-2-aldehyde-2-pyridylhydrazone | QAPH | 490 | 540 | 2 |
| Phenanthridine-2-aldehyde-2-pyridylhydrazone | PDAPH | 490 | 545 | 7 |
| Pyridine-2-aldehyde-2-quinolylhydrazone | PAQH | 470 | 535 | 660 |
| Quinoline-2-aldehyde-2-quinolylhydrazone | QAQH | 495 | 595 | 30 |
| Phenanthridine-2-aldehyde-2-quinolylhydrazone | PDAQH | 525 | 610 | 16 |
| Pyridine-2-aldehyde-2-phenanthrdinylhydrazone | PAPDH | 450 | 540 | 100 |
| Quinoline-2-aldehyde-2-phenanthrdinylhydrazone | QAPDH | 510 | 600 | 110 |
| Phenanthridine-2-aldehyde-2-phenanthrdinylhydrazone | PDAPDH | 580 | 620 | 230 |
| Benzimidazole-2-aldehyde-2-pyridylhydrazone | BAPH | 440 | 510 | 140 |
| 470B550enzimidazole-2-aldehyde-2-quinolylhydrazone | BAQH | 470 | 520 | 2000 |
| Benzimidazole-2-aldehyde-2-phenanthrdinylhydrazone | BAPDH | 480 | 530 | 440 |
| Phenyl-2-pyridylketone-2-pyridylhydrazone | PPKPH | 420 | 470 | 8 |
| Phenyl-2-pyridylketone-2-quinolylhydrazone | PPKQH | 470 | 550 | 450 |
| Phenyl-2-pyridylketone-2-phenanthrdinylhydrazone | PPKPDH | 490 | 575 | 1520 |

Table 1 lists the bis-(2-heteroaromatic)hydrazones prepared by Ryan et al, supra. and including their excitation and emission wavelengths and relative fluorescence properties.

Figure 3:
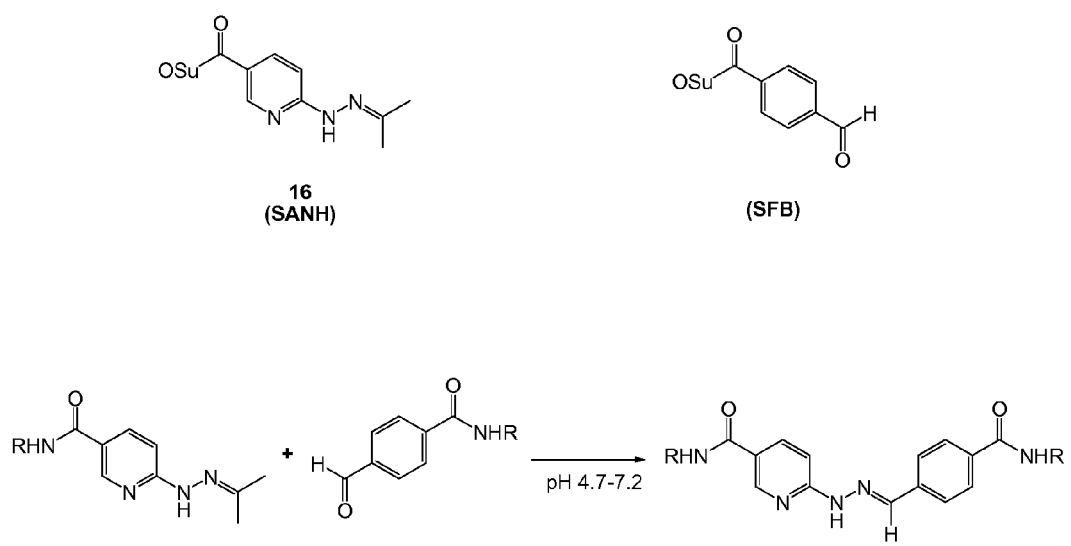
FIG. 3: Hydrazine and aldehyde succinimidyl ester reagents, SANH and SFB respectively, developed for modification of amino moieties on biomolecules and a diagrammatic representation of the conjugation of a hydrazine-modified biomolecules with a benzaldehyde-modified biomolecule.

Bifunctional hydrazine and carbonyl reagents to modify biomolecules have been prepared. FIG. 3 outlines this chemistry. The hydrazine/carbonyl bioconjugation couple has significant advantages over currently used maleimido/thiol couple in that both the aldehyde and hydrazine moieties are stable following incorporation on biomolecules, simple addition of an aldehyde-modified biomolecule to a hydrazine-modified biomolecule yields a stable hydrazone without the requirement of a reduction reaction to stabilize the bond, the stability of the functional groups allows conjugations to be performed at low concentrations, i.e. <100 microgram/mL and the chemistry has been engineered to prepare conjugates from all biomolecules.

Figure 4:
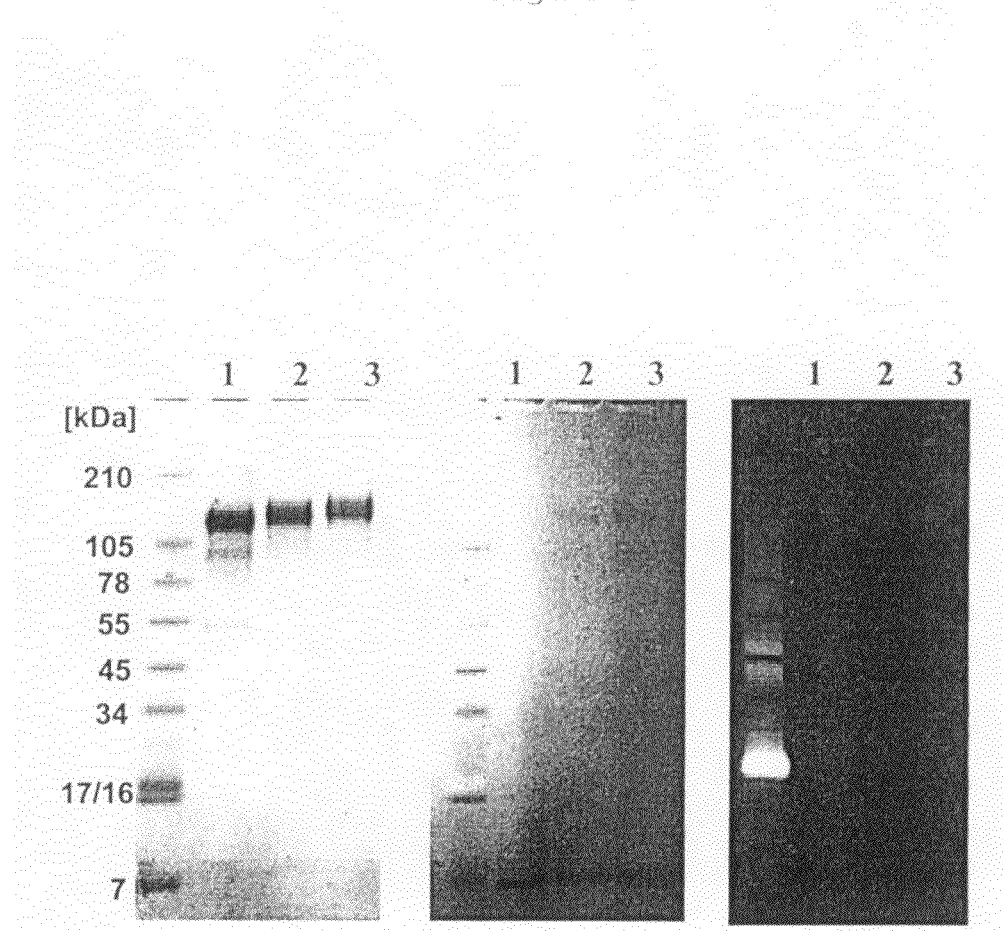
FIG. 4: (A) PAGE gel of the results of the conjugation of a 5'-benzaldehyde-modified oligonucleotide to a hydrazine-modified antibody visualized by coomassie blue (CB) staining; (B) the same gel visualized by UV backshadowing to visualize the oligonucleotide conjugated to the protein; (C) nitrocellulose membrane of the blotted conjugate following hybridization of the fluorescein-labeled complementary oligonucleotide demonstrating retention of hybridization functionality of conjugated oligonucleotide.

FIG. 4 shows the conjugation of an 5'-[4 formalbenzamide]-modified oligonucleotide to a hydrazine-modified antibody. The results demonstrate complete conversion of modified protein to conjugate by the simple addition of the stable 5'-[4 formalbenzamide]-modified oligonucleotide to the modified-hydrazine modified protein forming a stable hydrazone mediated conjugate.

The linkers have been prepared as reagents for the solid phase syntheses of peptides (hydrazino carboxylic acids) and oligonucleotides (aldehyde phosphoramidites). Aldehyde-modified deoxy and ribo-triphosphates have also been prepared and demonstrated to be incorporated into polynucleotide amplicons.

Figure 5:
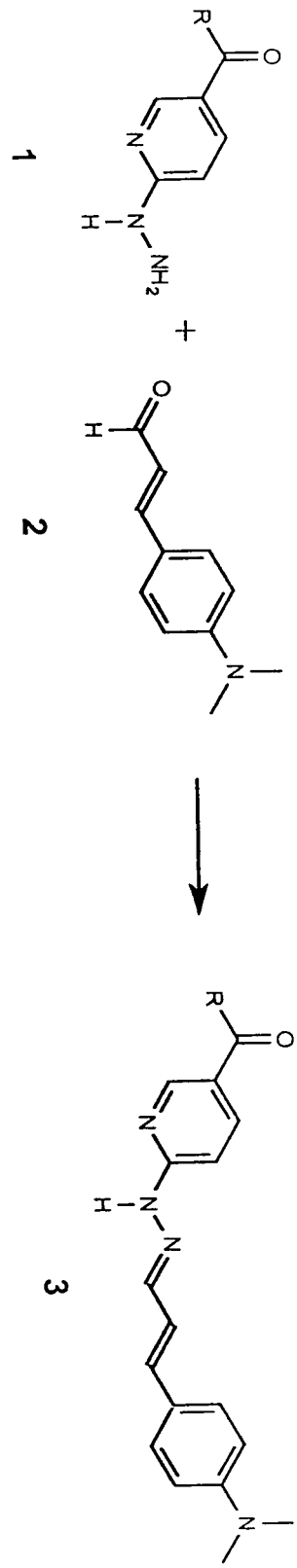
FIG. 5: A diagrammatic representation of fluorescent hydrazone (3) formed from 6-hydrazinonicotinic acid (1; R=OH) and 4-dimethylaminocinnamaldehyde (2)

In the initial demonstration of the fluorescence of conjugationally extended hydrazones, 6-hydrazinonicotinic acid (1) (Solulink Biosciences, San Diego, Calif.) was reacted with 4-dimethylcinnamaldehyde (2) (Aldrich Chemical Co., Milwaukee, Wis.) to yield fluorescent hydrazone (3) (FIG. 5). Hydrazone (3) absorbed at 397 nm and emitted at 508 nm a Stokes shift of 109 nm. Other hydrazones prepared from commercially available conjugationally extended hydrazines and aldehydes were prepared and their respective excitation and emission wavelengths are presented in Table 2 below. It should be noted that the Stokes shifts for hydrazones 2, 3 and 4 all are 100 nm or greater.

| | absorbance nm | emission nm |
|---|---|---|
| | 385 | 407 |

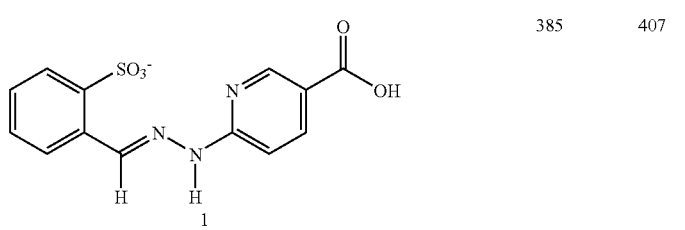

1

-continued

| | absorbance nm | emission nm |
|---|---|---|
| 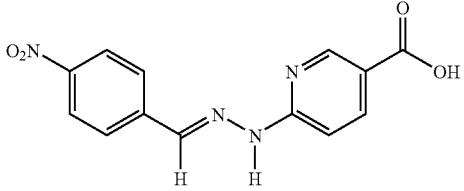 2 | 355 | 472 |
| 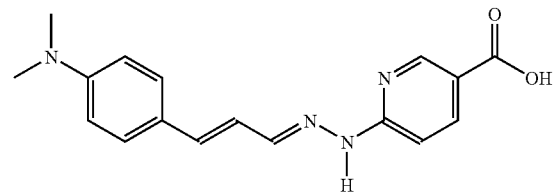 3 | 397 | 508 |
| 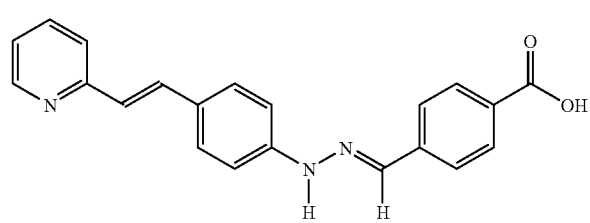 4 | 450 | 550 |

Table 2 shows the fluorescent hydrazones and their absorbance and emission maxima.

Figure 6:
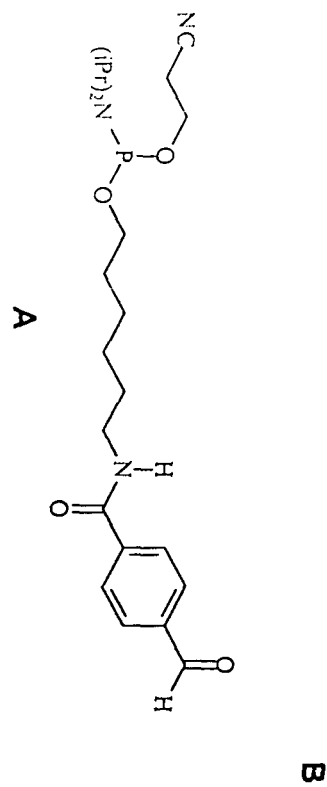
FIG. 6: (A) Chemical structure of benzaldehyde phosphoramidite used to incorporate benzaldehyde moieties on the 5'-terminus of oligonucleotides during their solid phase synthesis; (B) PAGE gel of purified oligonucleotide (Lane 1) and the product of the reaction of the oligonucleotide with trans-4-hydrazinostilbazole (1; Fluka Chemical Co.)
Figure 6:
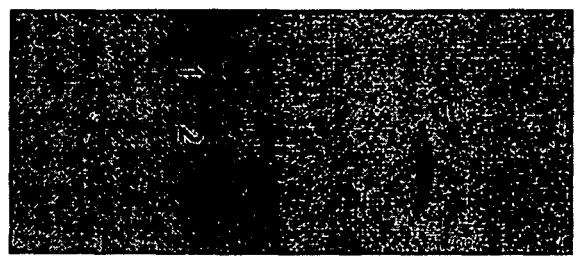
Figure 6:
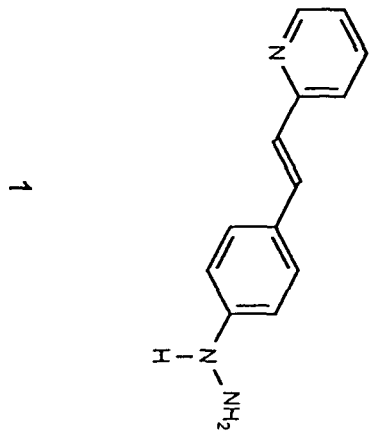
Figure 7:
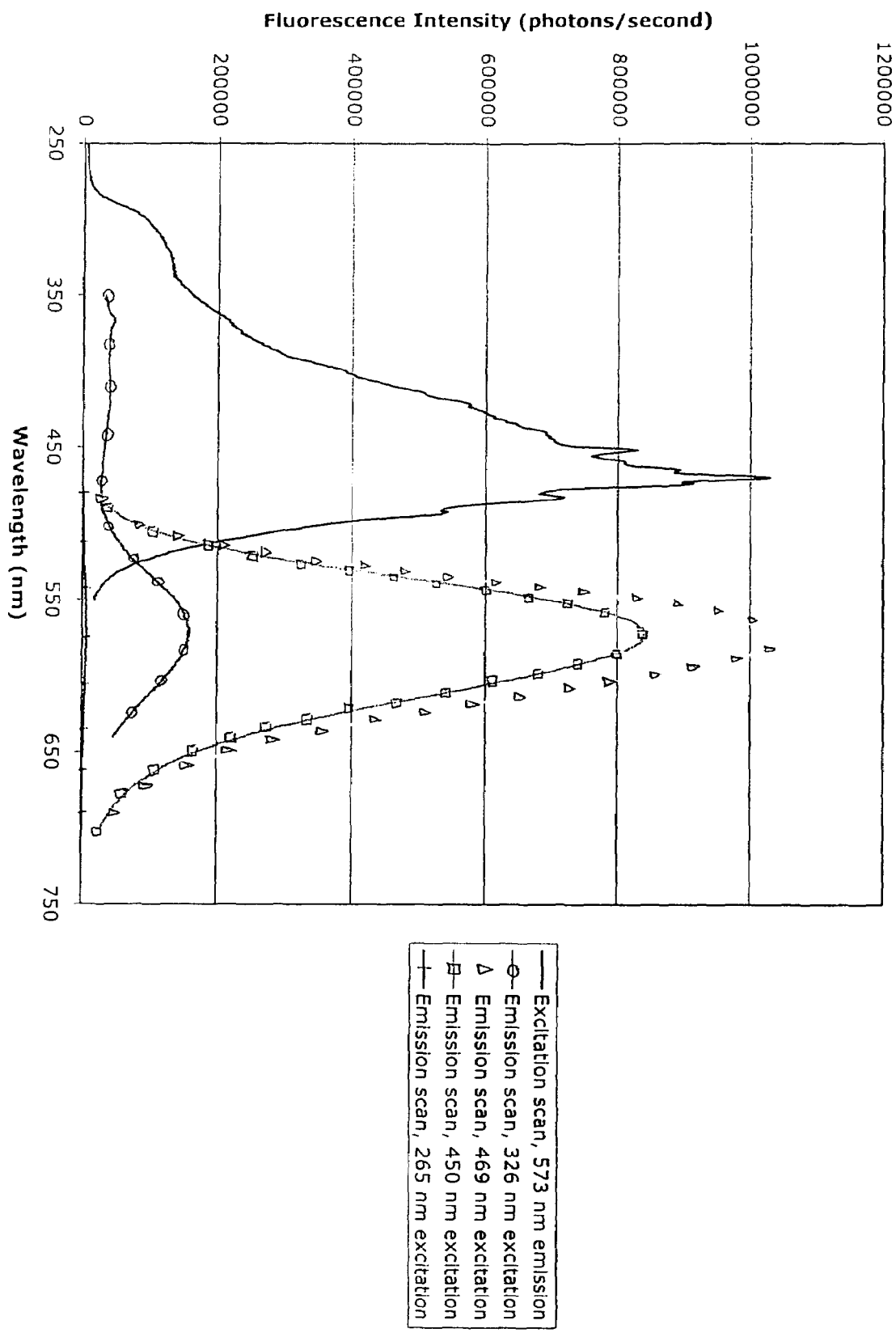
FIG. 7: Absorbance and emission spectra of a 22 mer oligonucleotide modified on the 5'-end with the hydrazone formed from the reaction of benzaldehyde and, trans-4'-Hydrazino-2-stilbazole.

In another demonstration benzaldehyde phosphoramidite has been prepared that is used to incorporate benzaldehyde moieties directly on the 5'-end of oligonucleotides during solid phase oligonucleotide synthesis. The incorporation of this moiety is accomplished with similar identical procedures and yields as incorporation of DMT-amino modified phosphoramidites. Reaction of an oligonucleotide with trans-4'-hydrazino-2-stilbazole dihydrochloride quantitatively yields a fluorescent oligonucleotide (FIG. 6). The emission and absorbance spectra of hydrazone (4) (see Table 2 above) linked to a 22 mer oligonucleotide are presented in FIG. 7.

Figure 8:
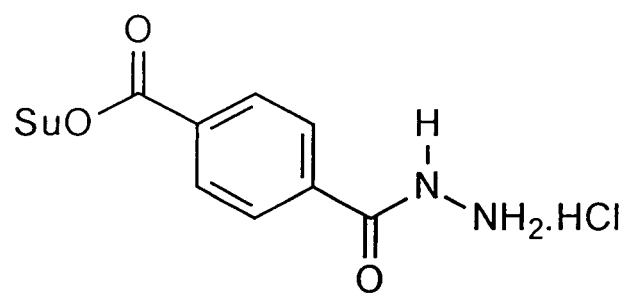
FIG. 8: Chemical structure of bifunctional hydrazido amine modification reagent SHTH.
Figure 9:
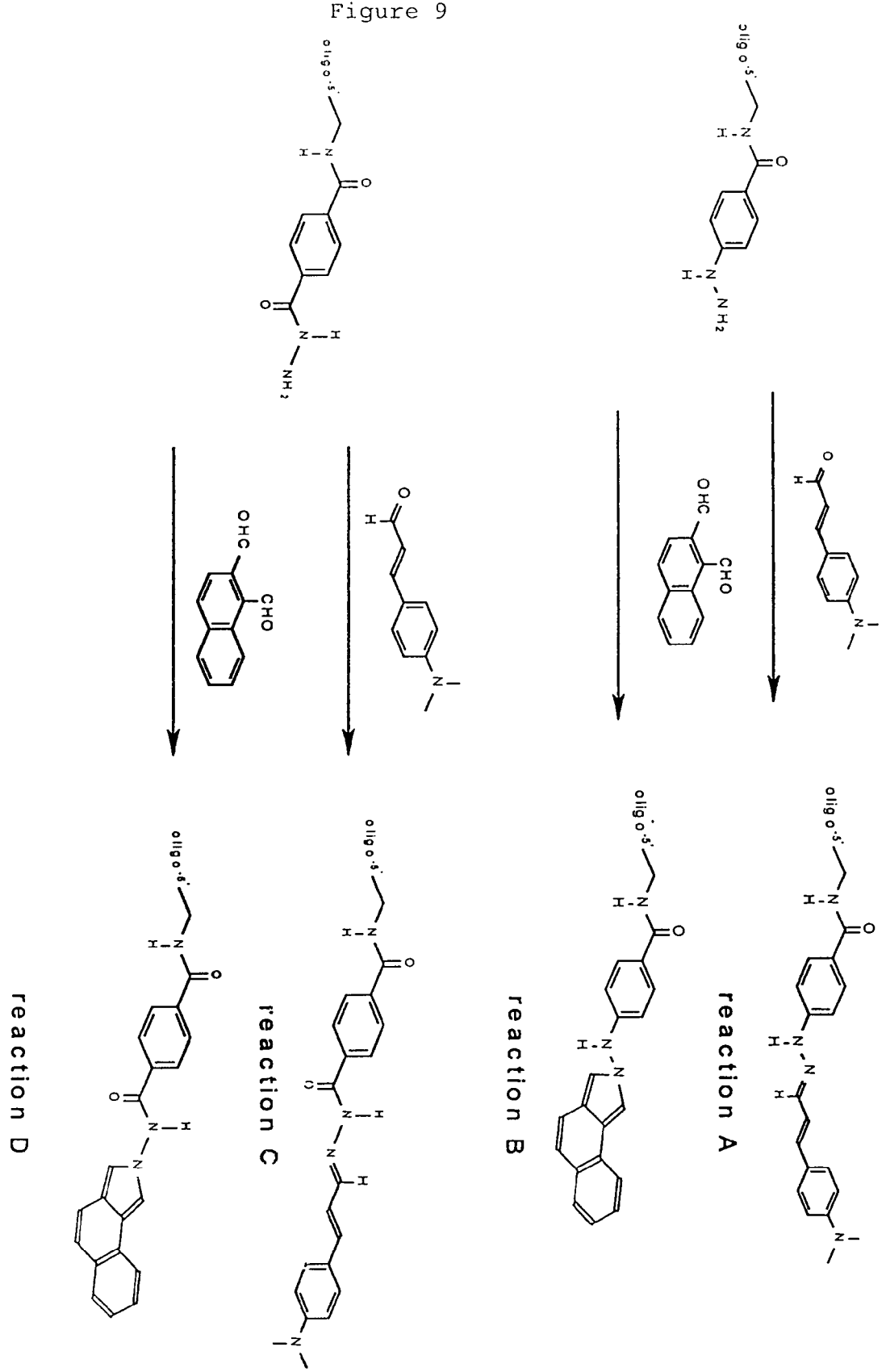
FIG. 9: A diagrammatic representation showing hydrazones prepared from conjugationally extended hydrazines and aldehydes form fluorescent species while hydrazones prepared from conjugationally extended hydrazides and aldehydes do not form substantially fluorescent species. 5'-(6-Hydrazinylpyridine)-modified oligonucleotide is reacted with 4-dimethylaminocinnamaldehyde (Reaction A) and naphthalene-1,2-dicarboxaldehyde (Reaction B) form fluorescent species. The hydrazone formed from the reaction of 5'-(6-hydrazidoterephalate)-modified oligonucleotide with 4-dimethylaminocinnamaldehyde is not fluorescent and the product with NDA forms a weakly fluorescent species based on the pyrollo-fused naphthalene product without conjugation through hydrazide moiety.

Methods have been developed to prepare both hydrazino- and hydrazido-modified oligonucleotides. Hydrazinopyridine-modified oligonucleotides can be prepared by the reaction of amino-modified oligonucleotides with SANH and hydrazido-modified oligonucleotides can be prepared using SHTH (FIG. 8). To demonstrate that hydrazones prepared from conjugationally extended hydrazines but not conjugationally extended hydrazides both oligonucleotides were reacted with 4-dimethylaminocinnamaldehyde (FIG. 9, reactions A and C) but only the hydrazine derived hydrazone was fluorescent. In another demonstration both hydrazino- and hydrazido-modified oligonucleotides were reacted with 1,2-naphthalene-dicarboxaldehyde (NDA; reactions B and D). It is known that amines react with NDA yield a fluorescent species. The products from the reaction of these oligonucleotides were both fluorescent however the hydrazine derived product absorbed and emitted qualitatively more intensely and at longer wavelengths than the hydrazido-modified oligonucleotide.

Figure 10:
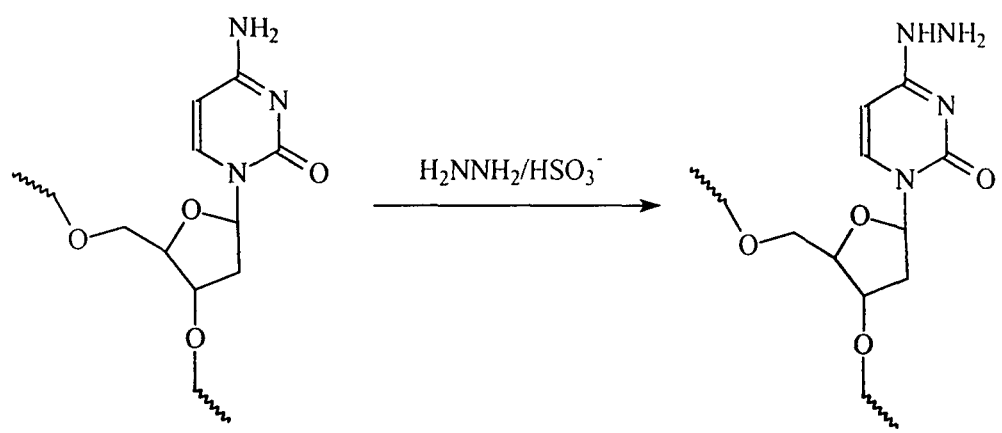
FIG. 10: A diagrammatic representation of the conversion of cytidine to 4-N-aminocytidine with hydrazine/bisulfite.
Figure 11:
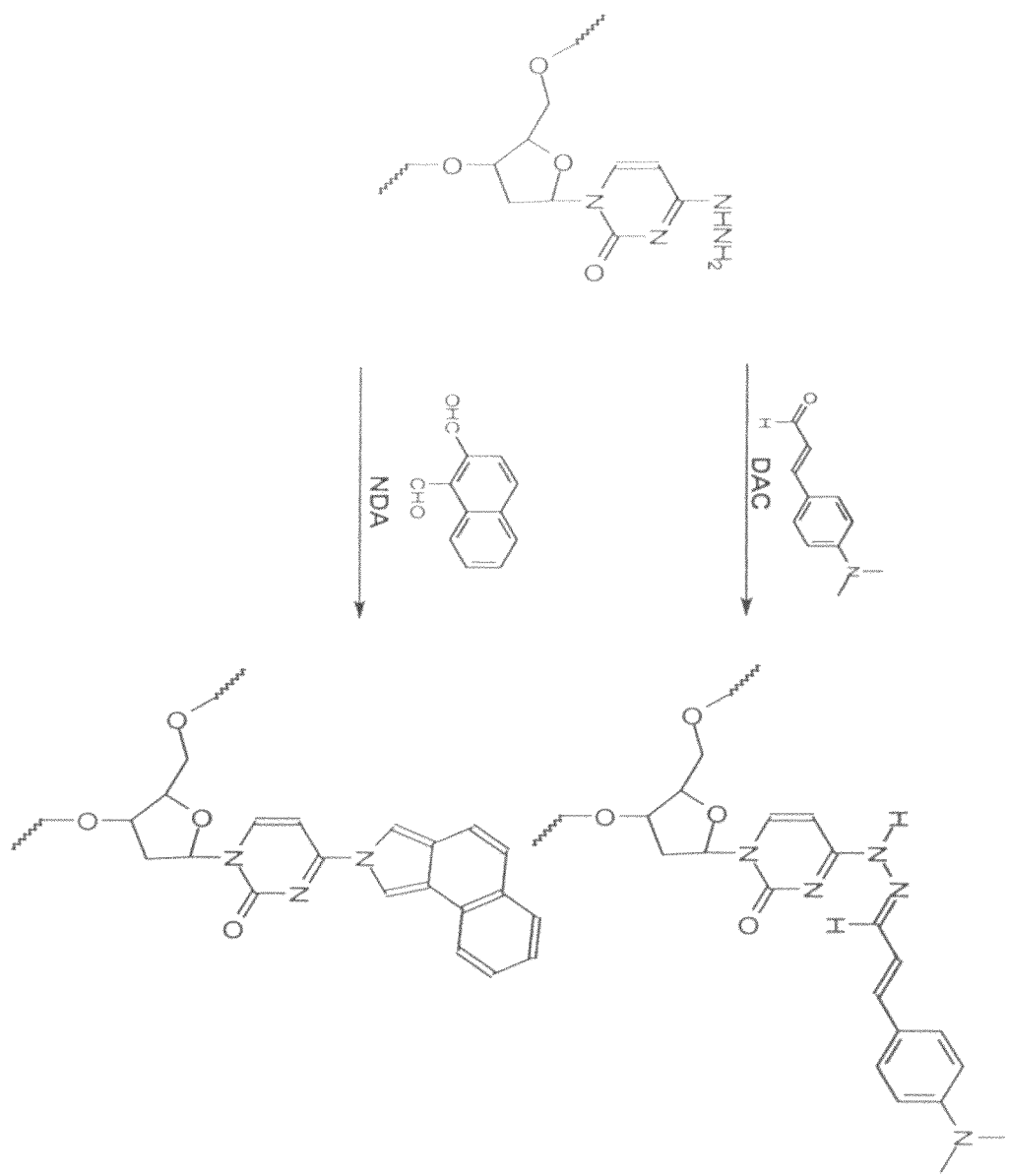
FIG. 11: A diagrammatic representation of the incorporation of fluorescence into DNA wherein salmon sperm DNA was treated with hydrazine/bisulfite to convert cytidine moieties to 4-aminocytidine, an aromatic hydrazine. The modified DNA was treated with dimethylaminocinnamaldehyde (DAC; top reaction; Lane 2) or naphthalene-1,2-dicarboxaldehyde (NDA; bottom reaction; Lane 4) and visualized following electrophoresis on an agarose gel (at left). Control reactions wherein untreated DNA was reacted with DAC and NDA were not fluorescent (Lanes 1 and 3 respectively)
Figure 11:
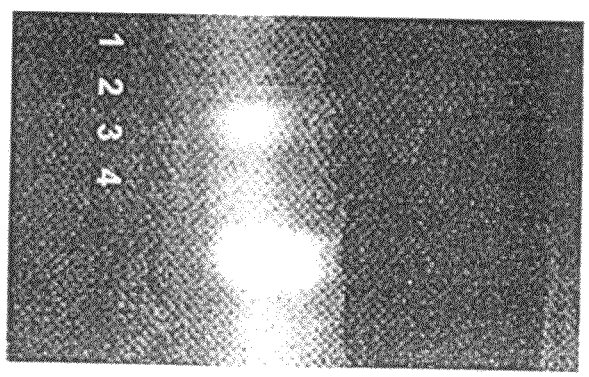

In another demonstration salmon sperm DNA was treated with hydrazine/bisulfite to convert cytidine moieties to 4-N-aminocytidine, an aromatic hydrazine (FIG. 10; Negishi, K., Harada, C., Ohara, Y., Oohara, K., Nitta, N. and Hayatsu, H., 4-N-aminocytidine, a nucleoside analog that has an exceptionally high mutagenic activity, Nucleic Acids Res. 1983, 11, 5223-33)). The reaction of the modified DNA with both 4-dimethylaminocinnamaldehyde and naphthalene-1,2-dicarboxaldehyde (NDA) yielded fluorescent DNA. (FIG. 11).

It should be noted that the hydrazine-modified cytidine is a component of the fluorophore and not solely a linkage point. It is anticipated that conjugationally extended aldehydes that yield hydrazones with more intensely fluorescent properties can be developed to convert reverse transcribed DNA to fluorescent species thereby using all natural triphosphates in the reverse transcription reaction and not substituted triphosphates whose incorporation is random and not quantitatively reproducible batch to batch.

Figure 12:
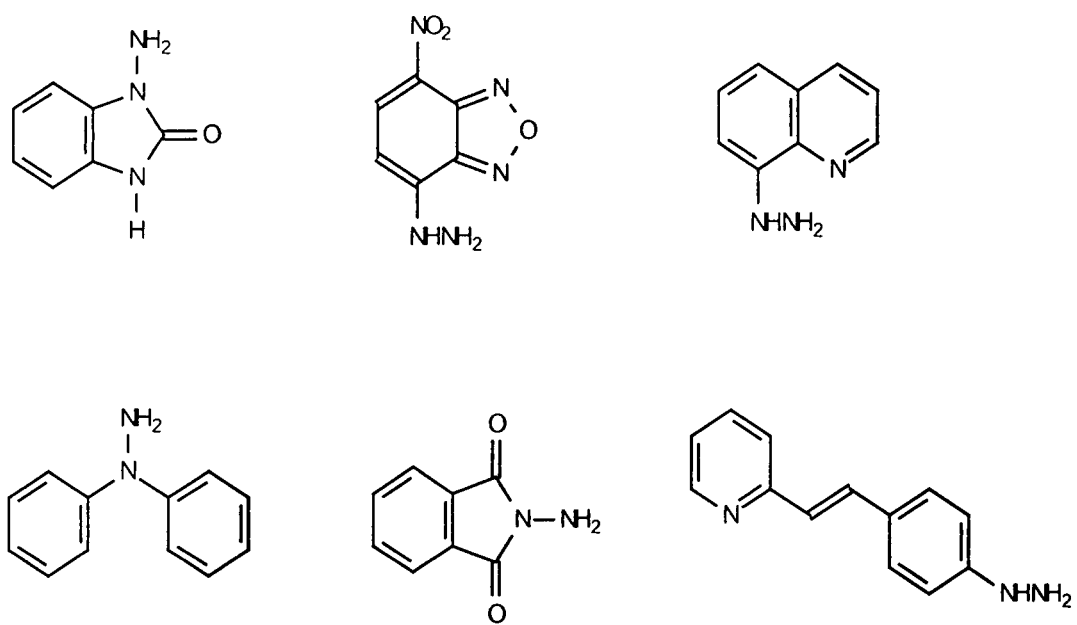
FIG. 12: Chemical structure of commercially available aromatic hydrazines.

A library of hydrazone fluorophores may be prepared from commercially available aromatic hydrazines and aldehydes using the methods described. FIG. 12 below presents structures of commercially available hydrazines that will be purchased to be reacted to form hydrazone fluorophores.

Figure 13:
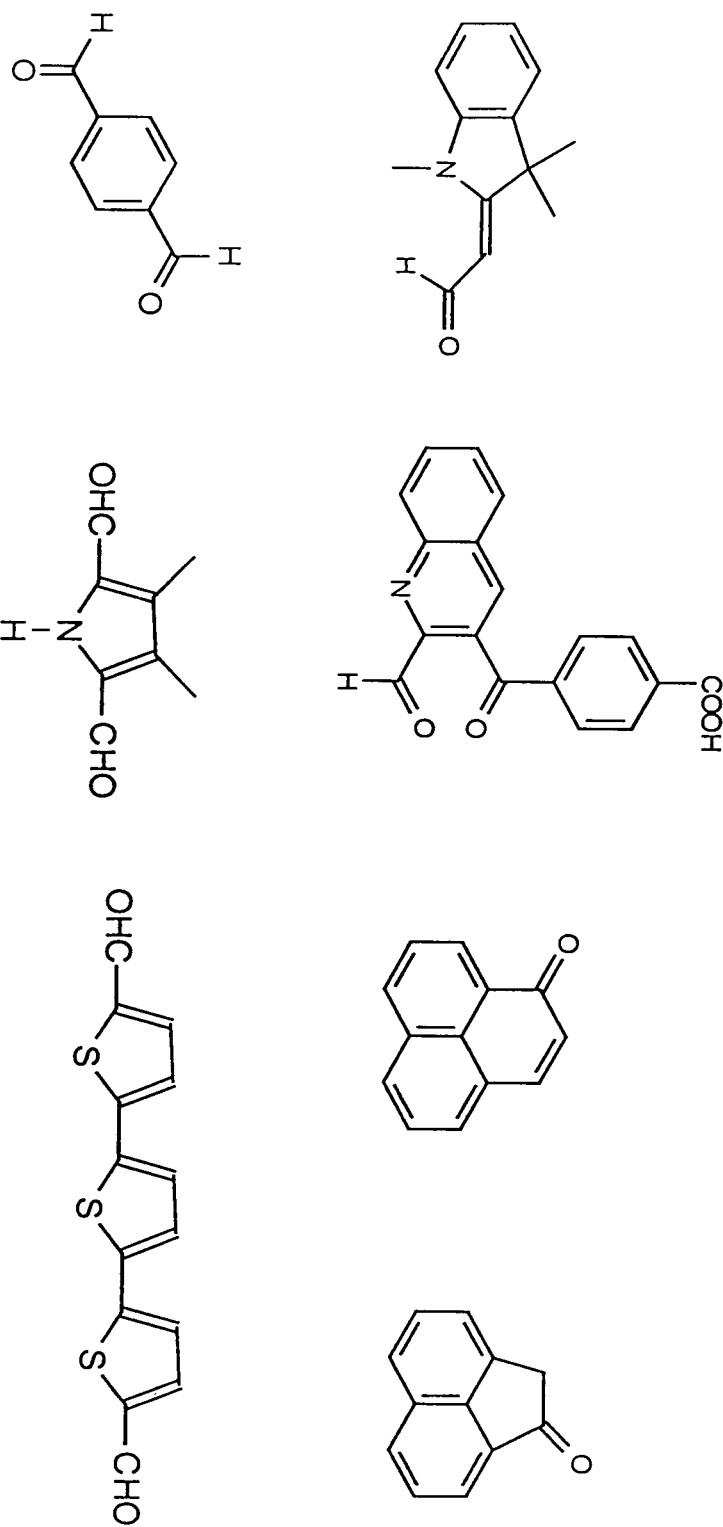
FIG. 13: Chemical structure of commercially available aldehydes.

FIG. 13 presents structures of commercially available aldehydes that will be purchased to be reacted to form hydrazone fluorophores.

Figure 14:
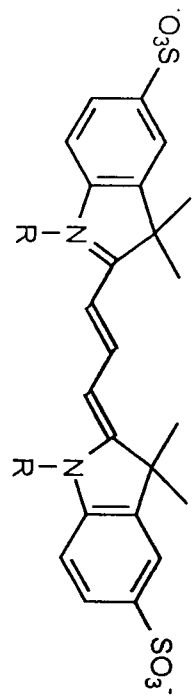
FIG. 14: Chemical structure of cyanine dyes Cy3 and Cy5.
Figure 14:
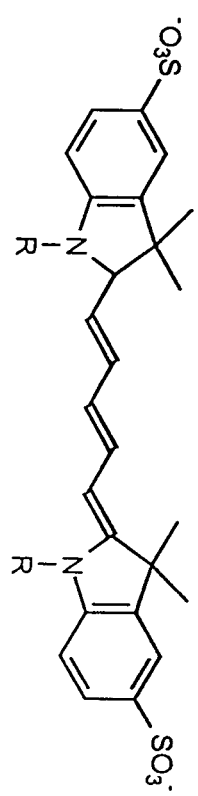

The initial pro-fluorophore structures targeted for syntheses in this program are based on cyanine dyes. These dyes are extremely sensitive and have been developed for a variety of commercial uses including life sciences applications as well as photographic uses (A. Mishra, R. K. Behera, P. K. Behera, .K. Mishra and G. B. Behera, Cyanines during the 1990's: A Review, Chem. Rev., 100:1973, 2000). FIG. 14 below presents the structures of the most used cyanine dyes, Cy3 and Cy5, for life science applications. These dyes are routinely used as reporter molecules in both gene and protein microarrays.

Figure 15:
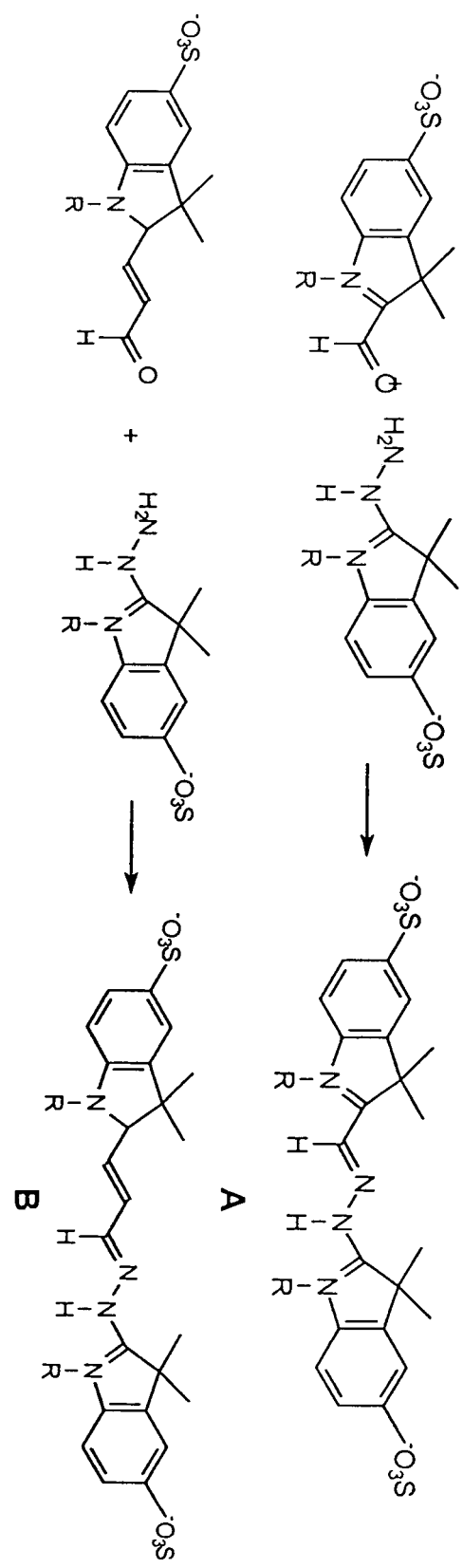
FIG. 15: Chemical structure of cyanine profluors and their parent fluorophores targeted for synthesis.

FIG. 15 presents aldehyde and hydrazine cyanine-based profluorophores and their parent fluorophores targeted for synthesis.

Figure 16:
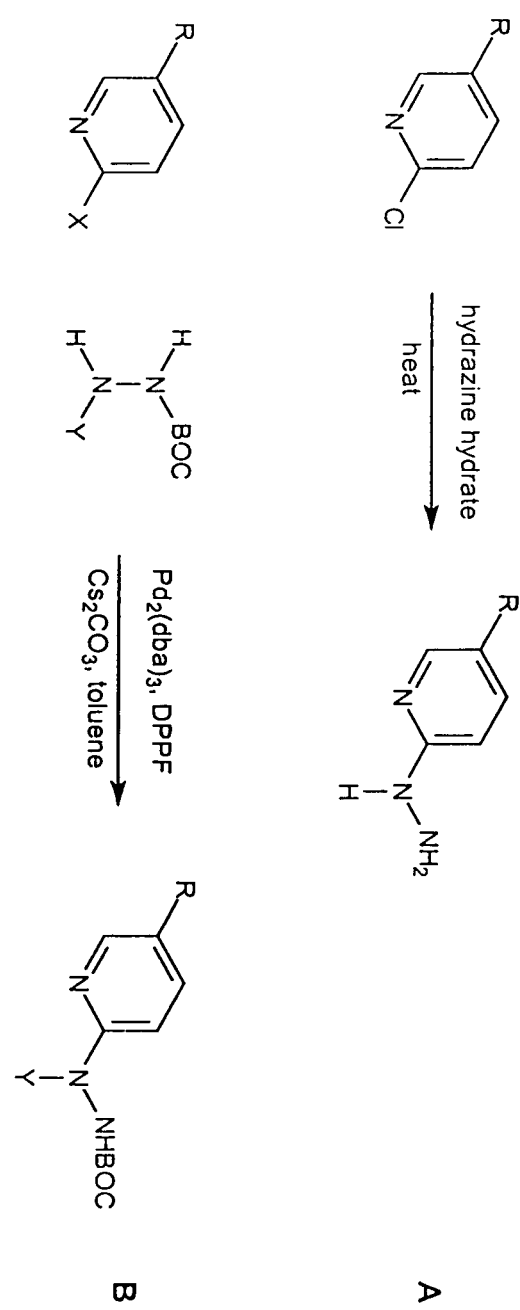
FIG. 16: A diagrammatic representation of the synthetic methods for the preparation of hydrazinoheterocyles.

Two methods have been developed for the preparation of hydrazino-substituted aromatic compounds (FIG. 16). The classical method for the synthesis of 2-hydrazinoheteroaromatic compounds is direct nucleophilic aromatic substitution of 2-chloro-heterocycles with hydrazine. Arterburn et al. (J. B. Arterburn, K. V. Rao, R. Ramdaa and B. R. Dible, Org. Lett. 2001, 3, 1351 and J. B. Arterburn, B. D. Bryant and D. Chen, Chem. Comm. 2003, 1890) have developed palladium-catalyzed protocols to convert 2-substituted bromo, chloro and trifloro substituted pyridines to 2-hydrazinylpyridines.

Aromatic aldehydes can be prepared by a variety of methods including direct oxidation of methyl-substituted aromatic moieties and reduction of aromatic nitrites. Aromatic aldehydes can be conjugationally extended using the Mannich reaction.

Figure 17:
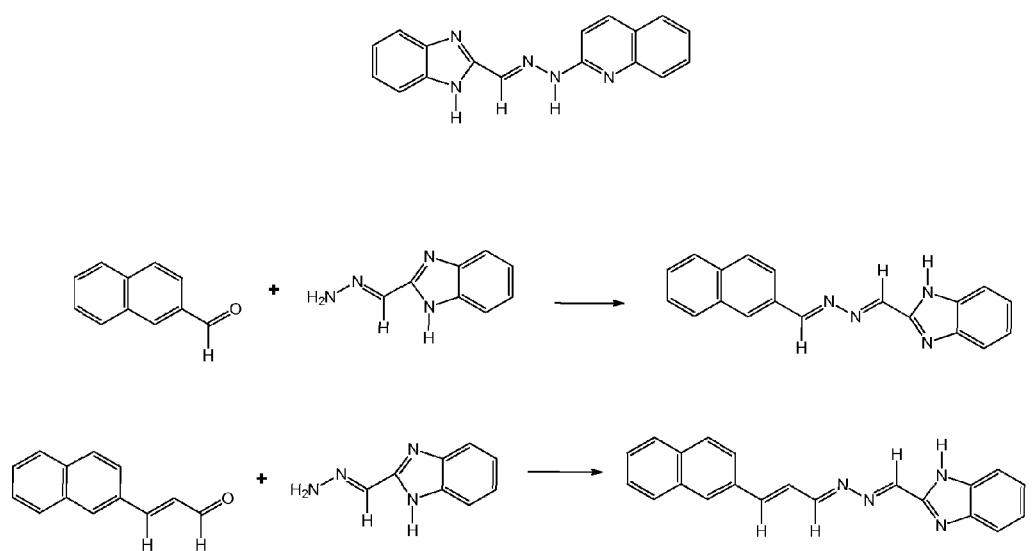
FIG. 17: Chemical structure of benzimidazole profluors and synthesis schemes of their parent fluorophores targeted for synthesis.
Figure 18:
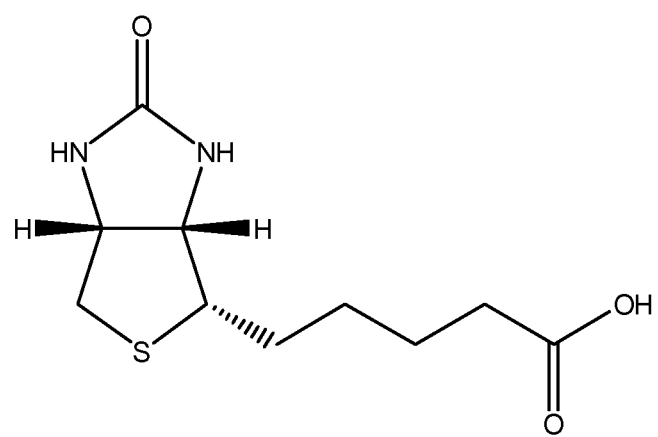
FIG. 18: Chemical structure of biotin.

Due to the fluorescence of benzimidazole-quinoline hydrazone (5) a variety of pro-fluorophores based on this parent core structure have been investigated. FIG. 17 presents target pro-fluorophores and their respective parent fluorophores.

Diverse libraries with varying fluorescent properties can be readily prepared as any carbonyl and any hydrazine prepared or commercially available can be combined to yield a fluorescent hydrazone. The excitation and emission characteristics desired can be tailored by incorporation of substituents such as dimethylamino, alkoxy and nitro groups.

The photophysical characteristics of the fluorophores may be observed using a QM-2 Spectrofluorimeter (Photon Technologies International, Inc.), with a nitrogen-dye laser/second harmonic generator excitation source. A Xe arc lamp may be utilized having excitation that allows for the collection of steady state excitation and emission spectra, the characterization of quantum yield, photo-bleaching, and an degradation of fluorescence from these species. The response of this instrument may be characterized by fluorescence quantum yield standards (i.e. quinine sulfate) to determine the quantum yield of the various fluorophores. The laser system with the laser-strobe detection attachment allows for the collection of sub nanosecond time-decays. The time decay curves may be analyzed to determine the excited-state lifetimes of these fluorophores.

In addition a Nd:YAG laser pumped OPO system, will allow for tunable excitation between 400 nm and 3000 nm. The detection system includes a Jobin-Yvon 0.5 m monochromator with both PMT and CCD detection. The CCD camera is sensitive in the visible and Near Infrared regions of the electromagnetic spectrum. This system may be used for the characterization of fluorophores in the far-red region of the visible spectrum and in the NIR region. The tunable excitation will provide a means to excite fluorophores, regardless of their absorption spectra in the visible/NIR regions The stability of the commercially available fluorophores has limited the full range of development of a variety of applications. The advantageous characteristics of this technology includes: elimination of the need to remove the excess second moiety from the in situ formed fluorescent species as it is either not fluorescent or has completely different fluorescent properties that do not interfere with detection of the new fluorescent species; increased efficiency of the formation of the fluorescent species >90%, in buffered aqueous media, pH 5.0-8.0; the ability to prepare a wide variety of fluorophores of different absorbance and emission wavelengths by varying the structures of the two moieties of the final fluorescent molecule; utilizing a linker moiety that may be incorporated on either of the pro-fluorescent species for covalent linking to a biomolecule or a surface; significant reduction in photobleaching or increased hydrolytic stability of the initial pro-fluorophore as has it will be in a lower energy state than fully conjugated fluorophores currently employed; and the development of fluorescent species having well separate spectral absorbance and emission properties, i.e. a Stoke's shift>100 nm.

Figure 19:
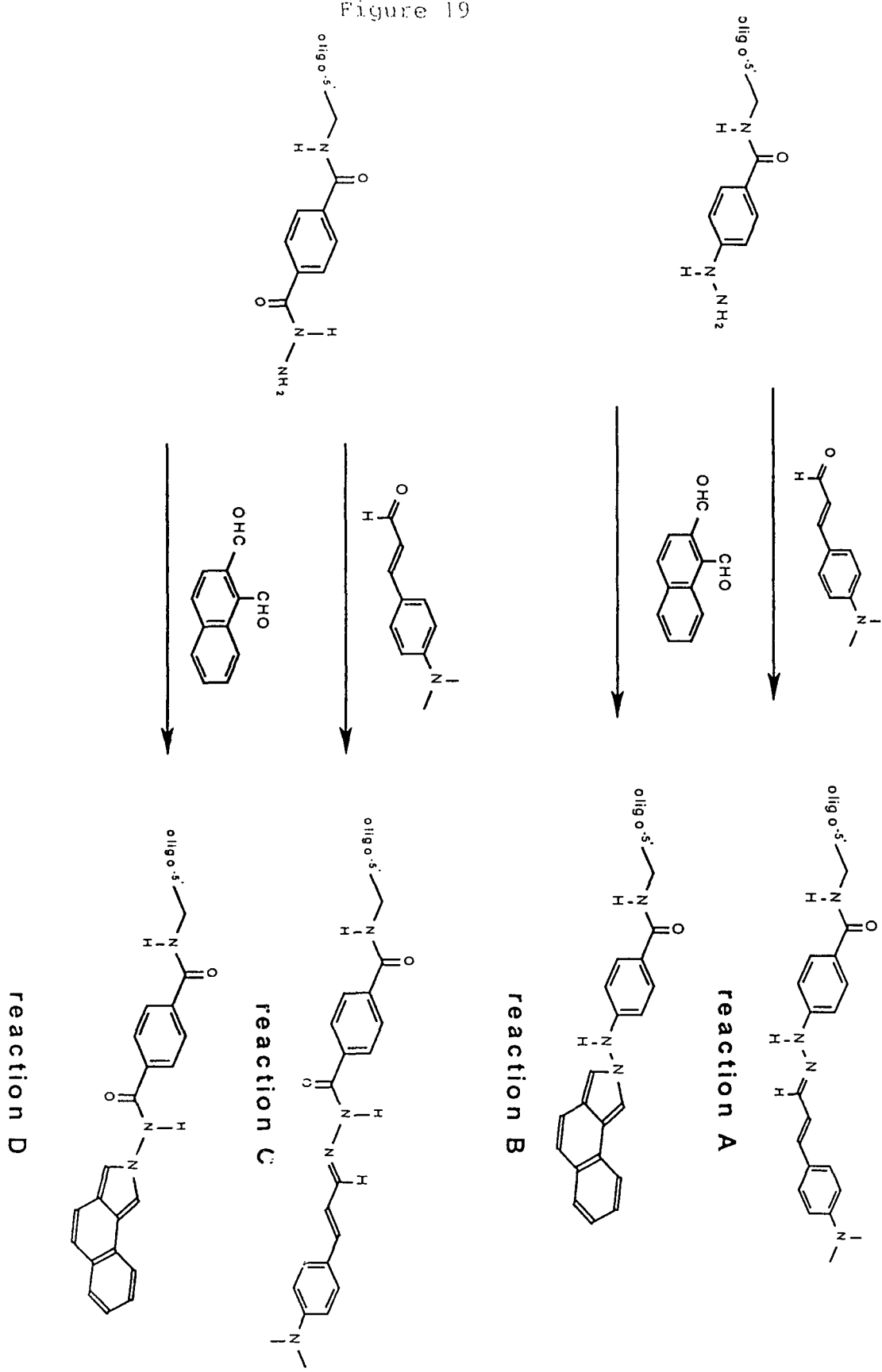
FIG. 19: A diagrammatic representation showing hydrazones prepared from conjugationally extended hydrazines and aldehydes that form fluorescent species while hydrazones prepared from conjugationally extended hydrazides and aldehydes do not form substantially fluorescent species. 5'-(6-Hydrazinylpyridine)-modified oligonucleotide is reacted with 4-dimethyl-aminocinnamaldehyde (Reaction A) and naphthalene-1,2-dicarboxaldehyde (Reaction B) form fluorescent species. The hydrazone formed from the reaction of 5'-(6-hydrazidoterephalate)-modified oligonucleotide with 4-dimethylaminocinnamaldehyde is not fluorescent and the product with NDA forms a weakly fluorescent species based on the pyrollo-fused naphthalene product without conjugation through hydrazide moiety.

U.S. patent application Ser. No. 60/546,104 to Schwartz incorporated herein in its entirety has described the in situ preparation of hydrazone fluorophores by the reaction of a conjugationally extended aldehyde with a conjugationally extended hydrazine one of which is linked to biomolecular probe such as an antibody or an oligonucleotide. FIG. 19 presents the reaction scheme for the reaction of a conjugationally extended hydrazine with a conjugationally extended aldehyde linked to an oligonucleotide forming an oligonucleotide linked fluorescent hydrazone. The scheme also presents results that demonstrated that the reaction is specific for a conjugationally extended hydrazine and not a hydrazide. In contrast to forming chromophore/fluorophores in situ the present invention incorporates a pre-formed chromophoric/fluorescent hydrazone into the linker comprising the ligand for direct spectrophotometric quantitation of the level of incorporation of the ligand when bound to a biomolecule such as a protein or nucleic acid.

Figure 20:
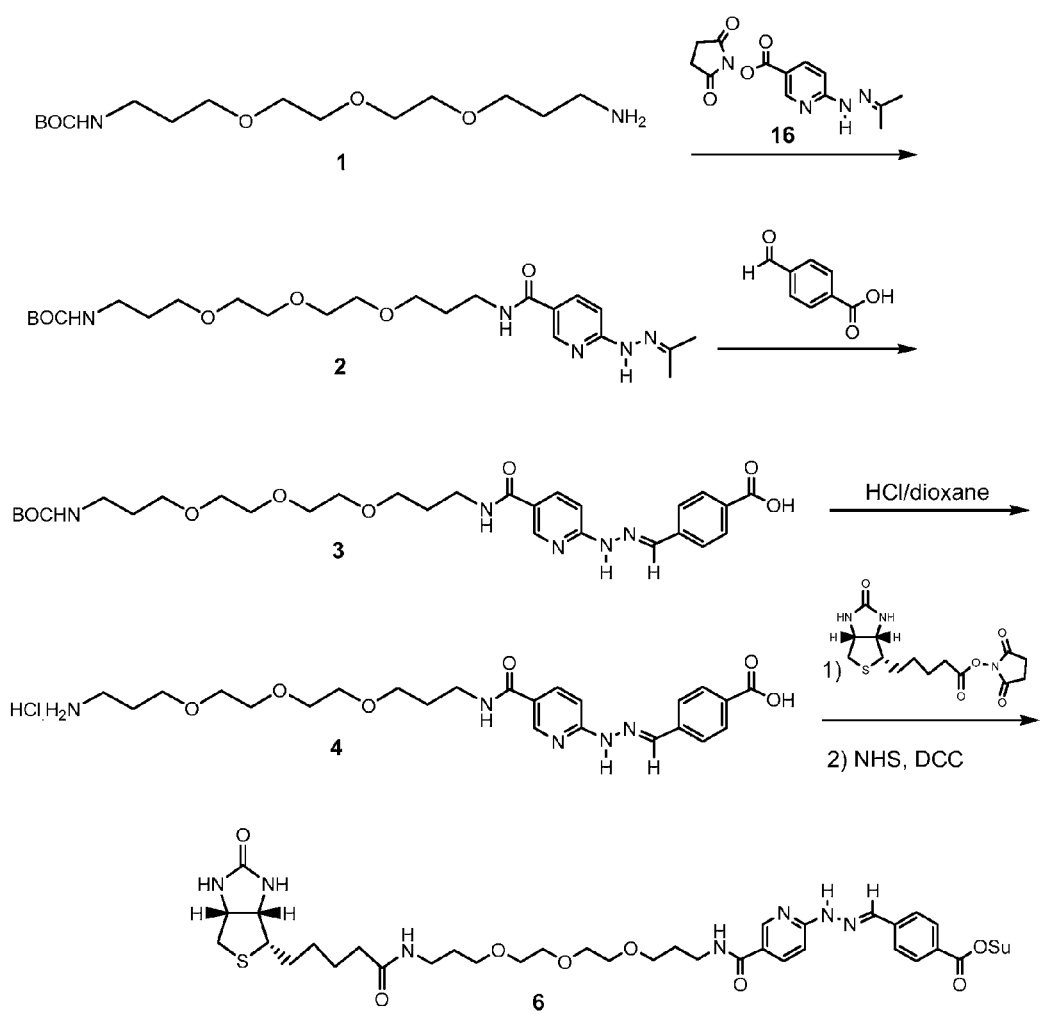
FIG. 20: A schematic representation of the synthesis of amino-reactive biotin/hydrazone chromophore 6.
Figure 21:
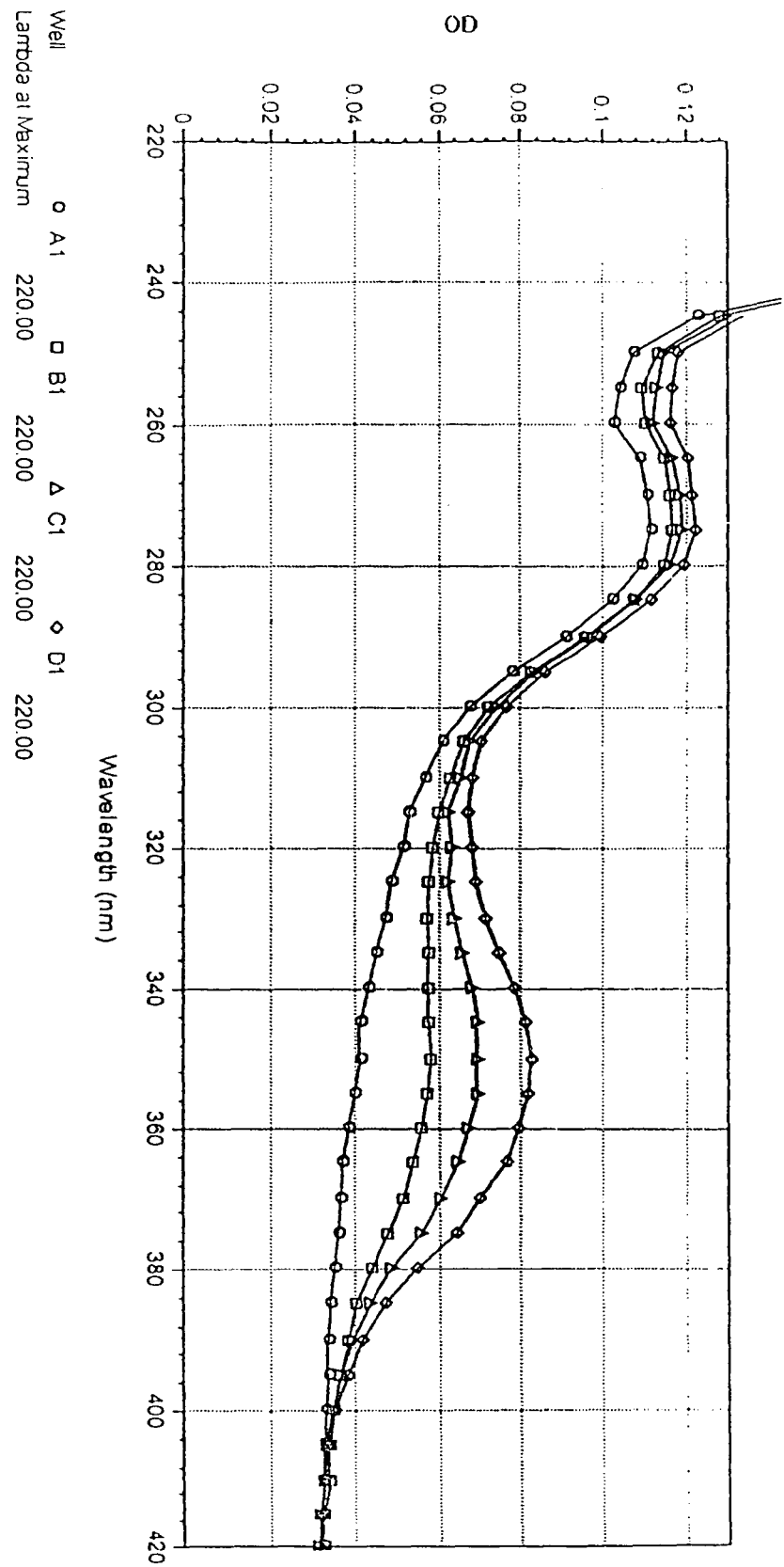
FIG. 21: A graph showing amino-reactive biotin/hydrazone chromophore 6 and overlaid spectra of equivalent amounts (20 μg) native bIgG and bIgG modified with 5×, 10× and 15× amino-reactive biotin/hydrazone chromophore 6 demonstrating the incorporation of chromophore/PEG4/biotin moiety by their absorbency at A354.

FIG. 20 presents the construction of an amino-reactive biotin moiety that has incorporated in its chain a chromophoric hydrazone for spectrophotometric quantitiation and a short PEG linker that is required to retain the binding affinity of biotin to streptavidin. This tri-functional molecule can be readily quantified spectrophotometrically following conjugation to a biomolecule because of its unique molar extinction coefficient (generally >20000) and its unique absorbance or fluorescence (generally at wavelengths greater than 300 nm and at frequencies having no, or only minimal, observable signals prior to conjugation). It is anticipated that more highly conjugated systems than presented in FIG. 20 will absorb at longer wavelengths with greater extinction coefficients or fluorescence allowing even greater sensitivity. FIG. 21 presents constructions of thiol and oxidized carbohydrate-reactive linkers of the present invention.

Figure 22:
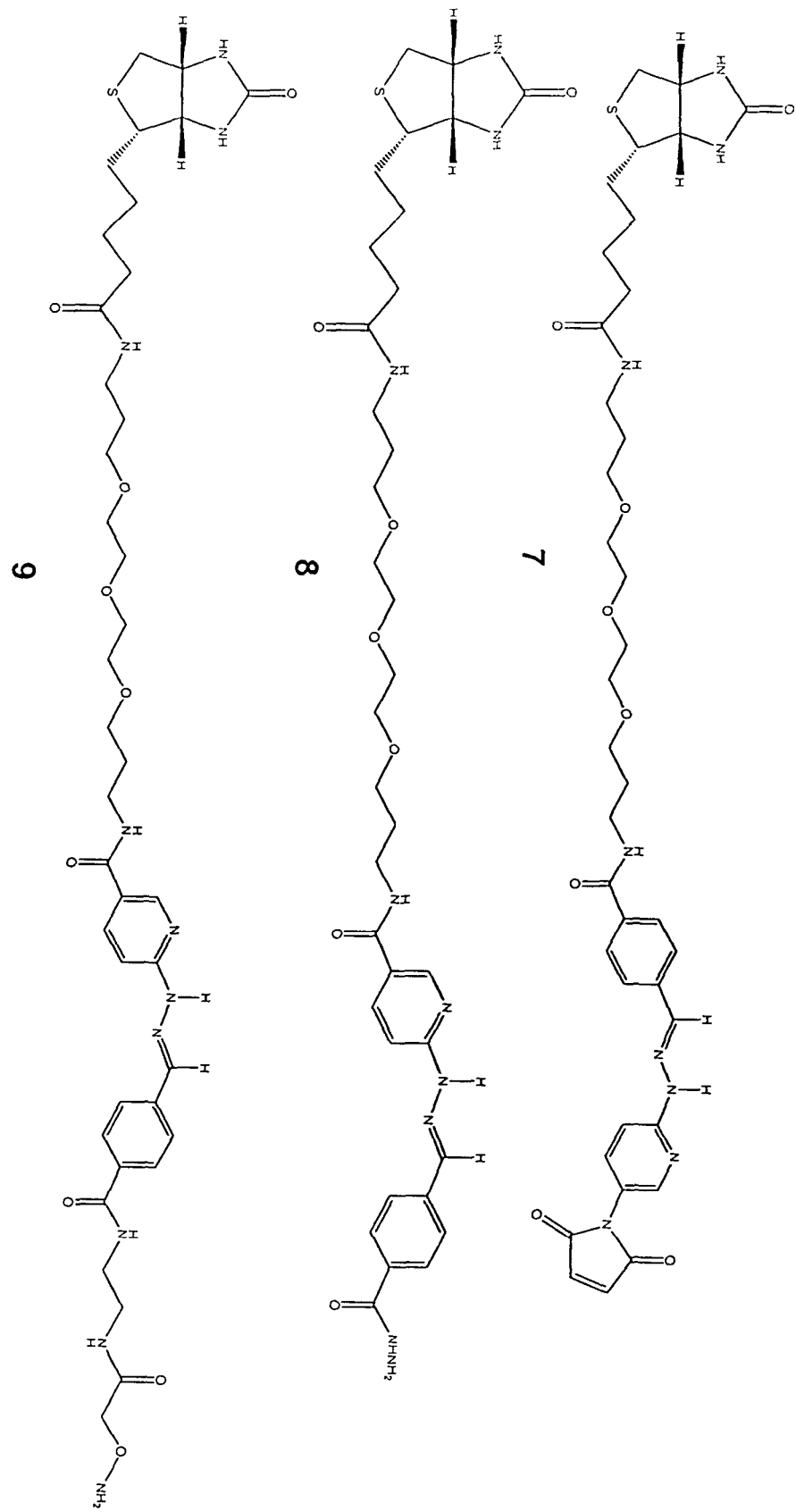
FIG. 22: Structure of a thiol-reactive chromophore linker of the present invention (7), aldehyde-reactive chromophore linker of the present invention (8) and an oxidized carbohydrate-reactive chromophore linker of the present invention (9)
Figure 23:
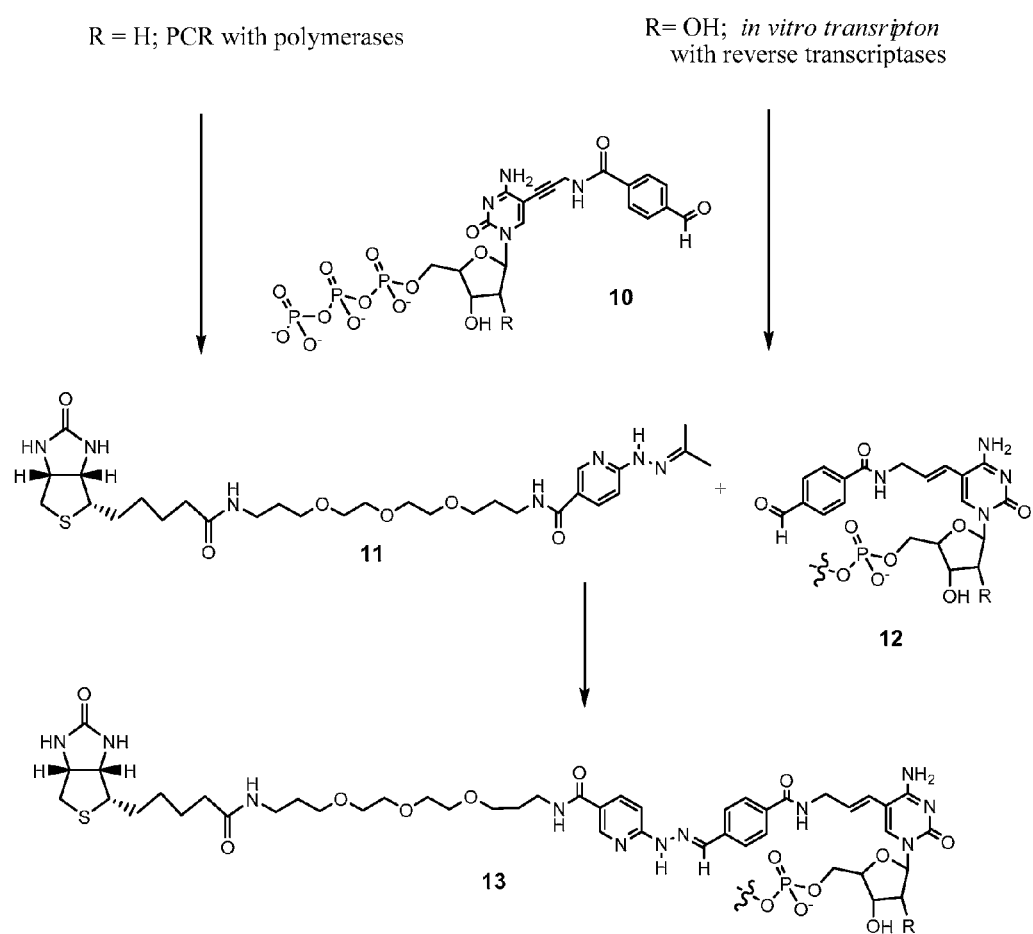
FIG. 23: A schematic representation of the incorporation of a conjugationally extended aldehyde cytosine triphosphate 10 in a DNA amplicon (R=H) or RNA amplicon (R=OH) and labeling the modified amplicon with a linker of the present invention 11

The incorporation of labels into nucleic acids such as cDNA or cRNA using polymerases and reverse transcriptases respectively for gene expression analysis by microarrays is a multi-step procedure that requires high levels of reproducibility so results can be reliably compared between experiments. One current method for labeling cDNA or cRNA is the use of a nucleoside modified to incorporate a biotin molecule on the minor groove side. One of the most commonly used methods to label and detect labeled cDNA and cRNA is using a biotinylated nucleoside triphosphate (NTP). As there are only labor-intensive methods to quantitate the level of biotin incorporation in the amplicon, the biotin-modified amplicon is used directly without quantitation. It would be extremely advantageous to be able to directly quantitate the level of biotin incorporated into cDNA or cRNA. FIG. 22 is a schematic diagram of the synthesis of a nucleoside triphosphate modified with a conjugationally extended aldehyde such as a benzaldehyde moiety and to label the amplicon after elongation by reaction with a biotinylated conjugationally extended hydrazine. U.S. Pat. No. 6,686,461 to D. Schwartz and R. Hogrefe which is incorporated herein by reference in its entirety more fully discloses this synthesis. The chemistry described herein is advantageous in that the formation of the hydrazone is high yielding at near stoichiometric amounts, a chromophore is formed that will allow batch-to-batch quantitiation of levels of incorporation of biotin and a short polyethylene linker is incorporated is necessary to retain the affinity of the biotin to its cognate receptor avidin.

In another protocol the amplicon may be hybridized prior to reaction with the biotin hydrazide and subsequently detected with a fluorescently-labeled avidin or anti-biotin antibody. The benzaldehyde-labeled amplicon can be quantitated by removing an aliquot and treating it with a hydrazide pro-fluorophore to form a fluorescent hydrazone and spectrophotometrically quantitating the level of aldehyde incorporation. This may be advantageous as the hybridization reaction will have minimal modification resulting in less sterically encumbered hybridization.

In use the linker moiety reacts with a biomolecule such as an antibody under appropriate reaction conditions. The conjugate is then purified and the protein concentration determined. The number of biotin molecules/protein molecule is determined by observing the absorbance of a known concentration of the conjugate in solution at a wavelength>300 nm. The concentration of the chromophore and therefore the biotin is determined by dividing the absorbance reading by the extinction coefficient of the chromophore incorporated in the chain. This concentration is divided by the mM concentration of the protein and the number of biotin molecules per conjugated is determined.

EXAMPLES

Example 1

Synthesis of Biotin/PEG/hydrazone succinimidyl ester 6 (FIG. 20)

PMR spectra were obtained on a Bruker 500 MHz NMR at NuMega Laboratories (San Diego, Calif.) and electrospray mass spectral data was obtained at HT Laboratories (San Diego, Calif.).

1. Synthesis of Mono-Boc-1,13-diamino-4,7,10-trioxatetradecane (1; (3-{2-[2-(3-Amino-propoxy)-ethoxy]-ethoxy}-propyl)-carbamic acid tert-butyl ester), Amine 1

To a solution of 4,7,10-trioxa-1,13-tridecanediamine (FIG. 20) (30 g; mmol) in dichloromethane (1000 mL) was added a solution of di-t-butyl dicarbonate (10 g; mmol; Aldrich Chemical Co., Milwaukee, Wis.) in dichloromethane (200 mL) over 2 h. The reaction mixture was stirred at room temperature for 4 hours. Thin layer chromatography (TLC, silica gel) using dichloromethane/methanol/triethylamine (90/10/1); ninhydrin development) indicated the presence of two new spots, a minor spot at Rf 0.8 ascribed to the bis-BOC product and a major spot at Rf (0.2) for the desired product. The reaction mixture was washed with water (4×500 mL) to remove the excess diamine and the organic phase was dried over magnesium sulfate, filtered and concentrated to give a viscous oil that was purified by flash chromatography over silica gel using DCM/MeOH/TEA (95/5/1) to give 10.5 g of desire Amine 1 as an oil.

2. Synthesis of ((3-{2-[2-(3-{[6-(N'-Isopropylidene-hydrazino)-pyridine-3-carbonyl]-amino}-propoxy)-ethoxy]-ethoxy}propyl)-carbamic acid tert-butyl ester), Hydrazone 2

To a solution of Amine 1 (1.05 g; 3.28 mmol) in DCM (20 mL) was added a solution of succinimidyl 6-hydrazinonicotiniate acetone hydrazone (0.951 g; 3.28 mmol; Solulink Biosciences, Inc., San Diego, Calif.) in DCM (10 mL). The reaction mixture was stirred at room temperature for 6 hours. Subsequently the reaction mixture was washed with water and brine. The organic phase was dried (magnesium sulfate), filtered and concentrated to give 1.2 g of Hydrazone 2 as a colorless thick oil.

3. Synthesis of (4-{[5-(3-{2-[2-(3-tert-Butoxy-carbonylamino-propoxy)-ethoxy]-ethoxy}-propylcarbamoyl)-pyridin-2-yl]-hydrazonomethyl}-benzoic acid), Hydrazone 3

To Hydrazone 2 (0.405 g: 0.81 mmol) in MeOH (5 mL) and 100 mM MES, 150 mM NaCl (5 mL) was added a solution of 4-carboxybenzaldehyde (0.121; 0.81 mmol) in MeOH (3 mL). The reaction mixture is allowed to stir at room temperature overnight. Copious precipitate formed. The reaction mixture was centrifuged and the solids were washed with a 1/1 solution of MeOH/MES. The solids were dried under vacuum to yield 0.42 g of Hydrazone 3 as a pale yellow solid and used directly in the next step.

4. Synthesis of (4-{[5-(3-{2-[2-(3-Amino-propoxy)-ethoxy]-ethoxy}-propylcarbamoyl)-pyridin-2-yl]-hydrazonomethyl}-benzoic acid hydrochloride salt), chromophore Hydrazone 4

A solution of Hydrazone 3 (0.388 g; 0.66 mmol) in dioxane (15 mL) was prepared with heating. The solution was cooled to room temperature and 4 N HCl in dioxane (4 mL; Aldrich Chemical Co., Milwaukee, Wis.) was added succinimidyl and the reaction was stirred at room temperature for 16 h. A precipitate formed on stirring. The reaction mixture was centrifuged and the solids were washed with dioxane (3×10 mL). The solids were resuspended in dioxane and concentrated under vacuum to yield 240 mg of amino/PEG4/Hydrazone 4 as a pale yellow solid. Electrospray mass spec: expected m/e 487. found positive mode 488 (M+H), negative mode 486 (M−H) and 522 (M+Cl⁻).

5. Synthesis of Biotin/PEG4/chromophore succinimidyl ester 6 (5-(N'-{4-[2-(2,5-Dioxo-pyrrolidin-1-yl)-2-oxo-acetyl]-benzylidene}-hydrazino)-pyridine-2-carboxylic acid {3-[2-(2-{3-[5-(2-oxo-hexahydro-thieno[3,4-d]imidazol-4-yl)-pentanoylamino]-propoxy}-ethoxy)-ethoxy]-propyl}-amide)

To a solution of amino/PEG4/hydrazone 4 (0.780 g; 1.60 mmol) in DMF (25 mL) was added biotin succinimidyl ester (0.546 g; 1.60 mmol) followed by the addition of triethylamine (0.726 mL; 4.80 mmol). The solution was stirred at room temperature until complete as determined by silica gel TLC using DCM/MeOH/TEA (90/10/1) as eluant (developed by UV to visualize the pyridine chromophore and dimethylaminocinnamaldehyde/sulfuric acid/ethanol spray followed by heating to visualize the biotin moiety). To the reaction mixture N-hydroxysuccinimide (0.184 g; 1.60 mmol) and DCC (0.330 g; 1.60 mmol) were added and stirred at room temperature for 16 hours. The reaction mixture was concentrated to dryness and partitioned between DCM and water. The organic phase was further washed with brine, dried (magnesium sulfate), filtered and concentrated to give a yellow sticky solid. The solids were triturated with ethyl acetate. The solids were isolated by filtration to give 830 mg of a yellow solid. TLC (DCM/MeOH/TEA (90/10/1) indicated one major spot (visualized by UV and dimethylaminocinnamaldehyde/sulfuric acid/ethanol solution) and HPLC analysis (YMC C-18, 150×4.6 cm; 5 μm; 120 A; gradient mobile phase A: water/acetonitrile/trifluoroacetic acid (20/80/0.1), mobile phase B: 0.1% TFA in water; gradient 10% A/90% B to 100% A over 20 min; retention time 8.8 min, detection @A254 and A350. PMR (DMSO-$d_6$) δ: 11.64, s (1H), 8.65, d, (1H), 8.37 t, (1H) NH, 8.12 dd (1H), 7.95 and 8.11 ab system (4H), 7.73 t (1H) NH, 7.36 d (1H), 6.41 s (1H), 6.35 s (1H), 5.57 d (1H), 4.29 br. t (1H), 4.11 br. t (1H), 3.3-3.55 m (12H), 3.08 m (4H), 2.90 s (4H), 2.88 dd (1H), 2.57 d (1H), 2.03 t (2H), 1.75 m (2H), 1.59 m (2H), 1.2-1.5 m (8H). The extinction coefficient of Biotin/PEG4/chromophore succinimidyl ester 6 was determined by dissolving Biotin/PEG4/chromophore succinimidyl ester 6 (1.0 mg) in DMF (1 mL) and diluting into PBS. The absorbance maximum was A354 and the molar extinction coefficient was determined to be 23,250.

Example 2

Protein labeling with Biotin/PEG4/chromophore/succinimidyl ester 6

Bovine immunoglobulin (bIgG; Sigma Chemical Co., St. Louis, Mo.) was dissolved in modification buffer (100 mM phosphate, 150 mM NaCl, pH 7.2) to prepare a 5 mg/mL solution. A solution of Biotin/PEG4/chromophore/succinimidyl ester 6 (1 mg) dissolved in DMF (100 mL) was prepared. Three separate reactions were performed wherein 5 mole equiv., 10 mol equiv. and 15 mol equiv. of Biotin/PEG4/chromophore/succinimidyl ester 6 (1.3, 2.6 and 3.9 μL,) respectively were added to 0.5 mg bIgG solution. The reaction was allowed to incubate at room temperature for 2 hours. The reaction mixtures were desalted into PBS using Biomax diafiltration apparatuses (Millipore, Inc., Bedford, Mass.). Protein concentrations of all the modified proteins were determined using the BCA assay (Pierce Chemical Co., Rockford, Ill.). Spectral analyses of each product were performed by diluting 20 mg of modified protein to 100 mL in PBS. The number of moles of chromophore incorporated was calculated by determining the absorbance of the protein at A354 dividing by the molar extinction coefficient, i.e. 29000, of the chromophore. The overlaid spectra of the products as well as unmodified IgG are present in FIG. 21A. The number of incorporated biotins in the modified proteins was further analyzed by the HABA assay (Pierce Chemical Co., Rockford, Ill.). The results, both tabular and graphically, from both the UV spectral assay and the HABA assay are presented below.

|     | IgG/HABA | IgG/A354 |
| --- | --- | --- |
| 5X  | 1.03 | 2.45 |
| 10X | 1.60 | 4.71 |
| 15X | 2.22 | 6.25 |

A further experiment to demonstrate retention of binding activity of the chromophore/biotinylated bIgG the modified proteins were incubated with streptavidin and the reaction products were analyzed by PAGE gel electrophoresis. FIG. 21B presents the results.

Example 3

Figure 24:
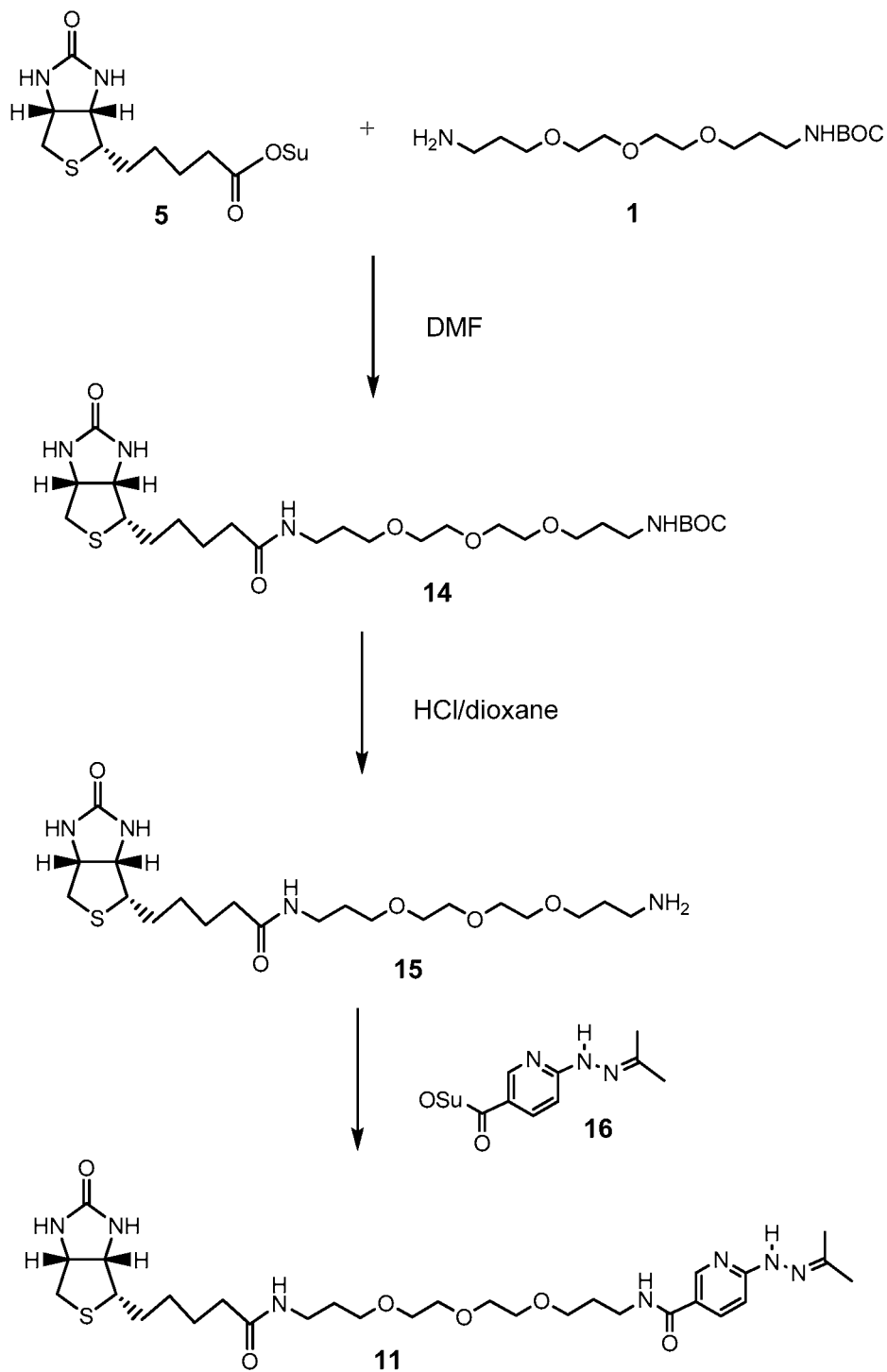
FIG. 24: Schematic representation of the synthesis of a linker of the present invention (11).

Synthesis of Biotin/PEG/hydrazone 10 (FIG. 24)

1. Synthesis of ({3-[2-(2-{3-[5-(2-Oxo-hexahydro-thieno[3,4-d]imidazol-4-yl)-pentanoylamino]-propoxy}-ethoxy)-ethoxy]-propyl}-carbamic acid tert-butyl ester), 1-biotinamido/PEG/BOC-amino 14

To a solution of Amine 1 (0.544 g; 1.70 mmol) in DMF (15 mL) was added a solution of biotin succinimidyl ester (0.580 g; 1.70 mmol) in DMF followed by the addition of TEA (0.75 mL; 5.09 mmol). The reaction mixture was stirred at room temperature for 16 h. The solvent was removed on the rotavap and the residue was partitioned between DCM and water. The organic phase was further washed with brine, dried (magnesium sulfate), filtered and concentrated to give 415 mg of 1-biotinamido/PEG/BOC-amino 14 as an amorphous solid. The product was a single spot by TLC (DCM/MeOH/TEA (90/10/1); developed by dimethylcinnamaldehyde/ethanol/sulfuric acid/heat to visualize the biotin moiety). The product was used directly in the next step.

2. Synthesis of (5-(2-Oxo-hexahydro-thieno[3,4-d]imidazol-4-yl)-pentanoic acid (3-{2-[2-(3-amino-propoxy)-ethoxy]-ethoxy}-propyl)-amide), 1-biotinamido/PEG/amino 15

To a solution of 1-biotinamido/PEG/BOC-amino 14 (400 mg; 0.73 mmol) was dissolved in dioxane (20 mL) with mild heating. The solution was cooled to room temperature and a solution of 4 N HCl in dioxane (10 mL; Aldrich Chemical Co., Milwaukee, Wis.) was added. The reaction was stirred for 14 h. The solvent was removed on the rotavap and the residue was co-evaporated twice from dry dioxane. The product, 1-biotinamido/PEG/amino 15, was used directly without purification.

3. Synthesis of (5-(N'-Methylene-hydrazino)-pyridine-2-carboxylic acid {3-[2-(2-{3-[5-(2-oxo-hexahydro-thieno[3,4-d]imidazol-4-yl)-pentanoylamino]-propoxy}-ethoxy)-ethoxy]-propyl}-amide), 1-biotinamido/PEG/amido-6-hydrazino-4-nicotinamide 11

To a solution of 1-biotinamido/PEG/amino 15 (0.375 g; 0.78 mmol) in DMF (25 mL) was added a solution of SANH (0.225 g; 0.78 mmol) and triethylamine ((0.645 mL; 4.66 mmol)). The reaction mixture was stirred at room temperature for 16 h. The solvent was removed on the rotavap and the residue was partitioned between DCM and water. The organic phase was further washed with brine, dried (magnesium sulfate), filtered and concentrated to give 290 mg of 1-biotinamido/PEG/amido-6-hydrazino-4-nicotinamide 11 as an amorphous solid. The product was a single spot, Rf 0.33, by TLC (DCM/MeOH/TEA (90/10/1) developed by dimethylcinnamaldehyde/ethanol/sulfuric acid/heat to visualize the biotin moiety). Mass spectral data: exptd m/e 621; pos mod exptd m/e 622 (M+H). found 622 and exptd 644 (M+Na). found 644; neg mode exptd m/e (M−H) 620. found 620 and (M+Cl⁻) 656. found 656

The invention claimed is:

1. A spectrophotometrically quantifiable linker comprising of formula:

A-B-C-D wherein;
A represents an amino reactive moiety, a thiol reactive moiety, or a carbohydrate reactive moiety, comprising: N-hydroxysuccinimidyl; p-nitrophenyl; pentafluorophenyl; N-hydroxybenzotriazolyl; maleimido; α-haloacetamido; pyridylsulfide; or aminooxy moiety;
B represents a chromophoric or fluorescent hydrazone-containing moiety, wherein the hydrazone-containing moiety fluoresces, emits light, or precipitates a colored insoluble product upon enzymatic processing;
C represents a flexible linker comprising PEG; and
D represents biotin or a receptor ligand.

2. The spectrophotometrically quantifiable linker of claim 1, wherein the amino reactive moiety comprises: N-hydroxysuccinimidyl, p-nitrophenyl, pentafluorophenyl, or N-hydroxybenzotriazolyl moiety.

3. The spectrophotometrically quantifiable linker of claim 1, wherein the thiol reactive moiety comprises: maleimido, α-haloacetamido, or pyridylsulfide moiety.

4. The spectrophotometrically quantifiable linker of claim 1, wherein the carbohydrate reactive moiety comprises: aminooxy moiety.

5. The spectrophotometrically quantifiable linker of claim 1, wherein the receptor ligand comprises: a digoxigenin, a peptide, a peptide-S, a protein, an antibody, an oligonucleotide, or a complimentary oligonucleotide.

6. The spectrophotometrically quantifiable linker of claim 1, wherein a biomolecule is bound to the spectrophotometrically quantifiable linker via:
 i) the amino reactive moiety, thiol reactive moiety, or carbohydrate reactive moiety of said spectrophotometrically quantifiable linker; or
 ii) the receptor ligand of said spectrophotometrically quantifiable linker.

7. The spectrophotometrically quantifiable linker of claim 6, wherein the biomolecule comprises: a protein, a peptide, an oligonucleotide, a complimentary oligonucleotide, a polynucleotide, or combinations thereof.

8. The spectrophotometrically quantifiable linker of claim 6, wherein the biomolecule and the biotin or receptor ligand of the biomolecule-bound spectrophotometrically quantifiable linker comprises:
 i) a biotin/avidin pair;
 ii) a digoxigenin/anti-digoxigenin pair;
 iii) a peptide/anti-peptide antibody pair;
 iv) a peptide-S/ribonuclease pair;
 v) a complementary oligonucleotide pair; or
 vi) an antibody/ligand pair.

9. The spectrophotometrically quantifiable linker of claim 6, wherein the biomolecule is bound to the spectrophotometrically quantifiable linker via the amino reactive moiety, thiol reactive moiety, or carbohydrate reactive moiety of said spectrophotometrically quantifiable linker.

10. The spectrophotometrically quantifiable linker of claim 6, wherein the biomolecule is bound to the spectrophotometrically quantifiable linker via the receptor ligand of said spectrophotometrically quantifiable linker.

11. The spectrophotometrically quantifiable linker of claim 1, wherein:
 i) a first biomolecule is bound to the spectrophotometrically quantifiable linker via the amino reactive moiety, thiol reactive moiety, or carbohydrate reactive moiety of said spectrophotometrically quantifiable linker; and
 ii) a second biomolecule is bound to the spectrophotometrically quantifiable linker via the biotin or receptor ligand of said spectrophotometrically quantifiable linker.

12. The spectrophotometrically quantifiable linker of claim 11, wherein the first biomolecule, the second biomolecule, or both, comprises: a protein, a peptide, an oligonucleotide, a complimentary oligonucleotide, a polynucleotide, or combinations thereof.

13. The spectrophotometrically quantifiable linker of claim 11, wherein the second biomolecule and the biotin or receptor ligand of the biomolecule-bound spectrophotometrically quantifiable linker comprises:
 i) a biotin/avidin pair;
 ii) a digoxigenin/anti-digoxigenin pair;
 iii) a peptide/anti-peptide antibody pair;
 iv) a peptide-S/ribonuclease pair;
 v) a complementary oligonucleotide pair; or
 vi) an antibody/ligand pair.

14. The spectrophotometrically quantifiable linker of claim 1, wherein the flexible linker comprising PEG has no less than 8 carbon atoms and no more than 34 carbon atoms.

15. The spectrophotometrically quantifiable linker of claim 1, wherein the linker is (5-(N'-{4-[2-(2,5-dioxo-pyrrolidin-1-yl)-2-oxo-acetyl]-benzylidene}-hydrazino)-pyridine-2-carboxylic acid {3-[2-(2-{3-[5-(2-oxo-hexahydro-thieno[3,4-d]imidazol-4-yl)-pentanoylamino]-propoxy}-ethoxy)-ethoxy]-propyl}-amide).

16. The spectrophotometrically quantifiable linker of claim 1, wherein the chromophoric or fluorescent hydrazone-containing moiety comprises: an aryl moiety, a heteroaryl moiety, a heterocyclic moiety, or combinations thereof.

17. The spectrophotometrically quantifiable linker of claim 16, wherein the aryl moiety, the heteroaryl moiety, or the heterocyclic moiety comprises a ring fusion.

18. The spectrophotometrically quantifiable linker of claim 16, wherein the aryl moiety, the heteroaryl moiety, or the heterocyclic moiety comprises: a phenyl moiety, a naphthylene moiety, an anthracenyl moiety, a pyridinyl moiety, a quinolinyl moiety, a benzimidazolyl moiety, a pyrrolyl moiety, a benzopyrrolyl moiety, a thiophenyl moiety, or a cytidinyl moiety.

19. The spectrophotometrically quantifiable linker of claim 16, wherein the chromophoric or fluorescent hydrazone-containing moiety comprises:
 i) an aryl-containing hydrazone-containing moiety;
 ii) a heteroaryl-containing hydrazone-containing moiety;
 iii) a bis-aryl-containing hydrazone-containing moiety;
 iv) a bis-heteroaryl-containing hydrazone-containing moiety; or
 v) an aryl-heteroaryl-containing hydrazone-containing moiety.

20. The spectrophotometrically quantifiable linker of claim 1, wherein the chromophoric or fluorescent hydrazone-containing moiety comprises a conjugationally extended hydrazone-containing moiety.

21. The spectrophotometrically quantifiable linker of claim 20, wherein the conjugationally extended hydrazone-containing moiety comprises: an aryl moiety, a heteroaryl moiety, a heterocyclic moiety, or combinations thereof.

22. The spectrophotometrically quantifiable linker of claim 20, wherein the aryl moiety, the heteroaryl moiety, or the heterocyclic moiety comprises a ring fusion.

23. The spectrophotometrically quantifiable linker of claim 20, wherein the aryl moiety, the heteroaryl moiety, or the heterocyclic moiety comprises: a phenyl moiety, a naphthylene moiety, an anthracenyl moiety, a pyridinyl moiety, a quinolinyl moiety, a benzimidazolyl moiety, a pyrrolyl moiety, a benzopyrrolyl moiety, a thiophenyl moiety, or a cytidinyl moiety.

24. The spectrophotometrically quantifiable linker of claim 20, wherein the chromophoric or fluorescent conjugationally extended hydrazone-containing moiety comprises:
   i) a conjugationally extended aryl-containing hydrazone-containing moiety;
   ii) a conjugationally extended heteroaryl-containing hydrazone-containing moiety;
   iii) a conjugationally extended bis-aryl-containing hydrazone-containing moiety;
   iv) a conjugationally extended bis-heteroaryl-containing hydrazone-containing moiety; or
   v) a conjugationally extended aryl-heteroaryl-containing hydrazone-containing moiety.

* * * * *